(12) United States Patent
Ziv et al.

(10) Patent No.: US 9,339,363 B2
(45) Date of Patent: May 17, 2016

(54) MANAGEMENT OF URINARY INCONTINENCE IN FEMALES

(75) Inventors: Elan Ziv, Ramat-Gan (IL); Amir Perle, Haifa (IL); Eran Hirschowitz, Ramat-Gan (IL); Roni Shabat, Kibbutz Yizrael (IL); Idan Bauder, Carmiel (IL); Nir Sinai, Alon HaGalil-Doar-Na HaMovil (IL)

(73) Assignee: Kimberly Clark Worldwide, Inc., Neenah, WI (US)

( * ) Notice: Subject to any disclaimer, the term of this patent is extended or adjusted under 35 U.S.C. 154(b) by 829 days.

(21) Appl. No.: 12/680,575

(22) PCT Filed: Sep. 24, 2008

(86) PCT No.: PCT/IL2008/001292
§ 371 (c)(1),
(2), (4) Date: Mar. 29, 2010

(87) PCT Pub. No.: WO2009/044394
PCT Pub. Date: Apr. 9, 2009

(65) Prior Publication Data
US 2010/0217068 A1    Aug. 26, 2010

Related U.S. Application Data

(60) Provisional application No. 60/960,492, filed on Oct. 1, 2007.

(51) Int. Cl.
*A61F 2/00* (2006.01)
(52) U.S. Cl.
CPC ..................... *A61F 2/005* (2013.01)

(58) Field of Classification Search
USPC ...................................... 600/30, 32
See application file for complete search history.

(56) References Cited

U.S. PATENT DOCUMENTS

| | | |
|---|---|---|
| 2,141,040 A | 12/1938 | Holt |
| 2,146,574 A | 2/1939 | Ilay |
| 2,432,768 A | 12/1947 | Kurkjian |
| 2,938,519 A | 5/1960 | Marco |
| 3,138,159 A | 6/1964 | Schmidt |
| 3,646,929 A | 3/1972 | Bonnar |

(Continued)

FOREIGN PATENT DOCUMENTS

| | | |
|---|---|---|
| DE | 271657 | 3/1914 |
| DE | 19816349 | 10/1999 |

(Continued)

OTHER PUBLICATIONS

Response Dated Nov. 3, 2010 to Communication Pursuant to Article 94(3) EPC of Jul. 2, 2010 From the European Patent Office Re. Application No. 057188877.3.

(Continued)

*Primary Examiner* — Navin Natnithithadha
*Assistant Examiner* — Sunita Reddy
(74) *Attorney, Agent, or Firm* — Kimberly-Clark Worldwide, Inc.

(57) ABSTRACT

An apparatus for treating urinary incontinence, comprising: (a) a support section adapted for providing urethral support; (b) an anchoring section adapted for resisting movement of the apparatus; (c) a normally open expansion mechanism adapted to urge the support radially outwards; and (d) a conversion mechanism adapted to sharply and selectively reduce an outward urging of said support.

26 Claims, 20 Drawing Sheets

(56) References Cited

U.S. PATENT DOCUMENTS

| | | |
|---|---|---|
| 3,683,906 A | 8/1972 | Robinson |
| 3,789,828 A | 2/1974 | Schulte |
| 3,797,478 A | 3/1974 | Walsh et al. |
| 3,841,304 A | 10/1974 | Jones |
| 4,019,498 A | 4/1977 | Hawtrey |
| 4,019,499 A | 4/1977 | Fitzgerald |
| 4,139,006 A | 2/1979 | Corey |
| 4,142,649 A | 3/1979 | Forgey |
| 4,212,301 A | 7/1980 | Johnson |
| 4,307,716 A | 12/1981 | Davis |
| 4,428,365 A | 1/1984 | Hakky |
| 4,457,299 A | 7/1984 | Cornwell |
| 4,553,533 A | 11/1985 | Leighton |
| 4,726,805 A | 2/1988 | Sanders |
| 4,823,814 A | 4/1989 | Drogendijk et al. |
| 4,846,784 A | 7/1989 | Haber |
| 4,850,963 A | 7/1989 | Sparks et al. |
| 4,920,986 A | 5/1990 | Biswas |
| 5,007,894 A | 4/1991 | Enhorning |
| 5,014,722 A | 5/1991 | Bauer |
| 5,036,867 A | 8/1991 | Biswas |
| 5,041,077 A | 8/1991 | Kulick |
| 5,090,424 A | 2/1992 | Simon et al. |
| 5,224,493 A | 7/1993 | Sawan et al. |
| 5,224,494 A | 7/1993 | Enhorning |
| 5,336,208 A | 8/1994 | Rosenbluth et al. |
| 5,352,182 A | 10/1994 | Kalb et al. |
| 5,370,657 A | 12/1994 | Irie |
| 5,386,836 A | 2/1995 | Biswas |
| 5,417,226 A | 5/1995 | Juma |
| 5,483,976 A | 1/1996 | McLaughlin et al. |
| 5,603,685 A | 2/1997 | Tutrone, Jr. |
| 5,609,586 A | 3/1997 | Zadini et al. |
| 5,618,256 A | 4/1997 | Reimer |
| 5,659,934 A | 8/1997 | Jessup et al. |
| 5,671,755 A | 9/1997 | Simon et al. |
| 5,724,994 A | 3/1998 | Simon et al. |
| 5,755,906 A | 5/1998 | Achter et al. |
| 5,771,899 A | 6/1998 | Martelly et al. |
| 5,782,745 A | 7/1998 | Benderev |
| 5,785,640 A | 7/1998 | Kresch et al. |
| 5,788,664 A | 8/1998 | Scalise |
| 5,795,346 A | 8/1998 | Achter et al. |
| 5,894,842 A | 4/1999 | Rabin et al. |
| 6,013,023 A | 1/2000 | Klingenstein |
| 6,090,038 A | 7/2000 | Zunker et al. |
| 6,090,098 A | 7/2000 | Zunker et al. |
| 6,142,928 A | 11/2000 | Zunker et al. |
| 6,158,435 A | 12/2000 | Dorsey |
| 6,189,535 B1 | 2/2001 | Enhorning |
| 6,216,698 B1 | 4/2001 | Regula |
| 6,251,122 B1 | 6/2001 | Tsukernik |
| 6,413,206 B2 | 7/2002 | Biswas |
| 6,415,484 B1 | 7/2002 | Moser |
| 6,418,930 B1 | 7/2002 | Fowler |
| 6,428,467 B1 | 8/2002 | Benderev |
| 6,458,072 B1 | 10/2002 | Zunker |
| 6,460,542 B1 | 10/2002 | James |
| 6,461,215 B1 | 10/2002 | Kunz et al. |
| 6,478,726 B1 | 11/2002 | Zunker |
| 6,503,190 B1 | 1/2003 | Ulmsten et al. |
| 6,558,370 B2 | 5/2003 | Moser |
| 6,645,136 B1 | 11/2003 | Zunker et al. |
| 6,676,594 B1 | 1/2004 | Zunker et al. |
| 6,679,831 B1 | 1/2004 | Zunker et al. |
| 6,739,340 B1 | 5/2004 | Jensen et al. |
| 6,770,025 B2 | 8/2004 | Zunker |
| 6,808,485 B2 | 10/2004 | Zunker |
| 7,036,511 B2 | 5/2006 | Nissenkorn |
| 7,717,892 B2 | 5/2010 | Bartning et al. |
| 7,931,671 B2 | 4/2011 | Tenerz |
| 8,435,168 B2 | 5/2013 | Ziv et al. |
| 2002/0068023 A1 | 6/2002 | Davis |
| 2002/0083949 A1 | 7/2002 | James |
| 2002/0115906 A1 | 8/2002 | Miller |
| 2002/0120243 A1 | 8/2002 | Kraemer et al. |
| 2002/0138035 A1 | 9/2002 | Hull, Jr. |
| 2002/0156341 A1 | 10/2002 | Zunker |
| 2002/0156343 A1 | 10/2002 | Zunker |
| 2002/0183711 A1 | 12/2002 | Moser |
| 2003/0149334 A1 | 8/2003 | Ulmsten et al. |
| 2003/0149392 A1 | 8/2003 | Arnould |
| 2004/0054252 A1 | 3/2004 | Zunker |
| 2004/0078013 A1 | 4/2004 | Zunker et al. |
| 2004/0084054 A1 | 5/2004 | Kaseki et al. |
| 2004/0122285 A1 | 6/2004 | Zunker |
| 2004/0158122 A1 | 8/2004 | Guerquin |
| 2004/0199100 A1 | 10/2004 | LeMay et al. |
| 2005/0016545 A1 | 1/2005 | Nissenkorn |
| 2006/0100475 A1 | 5/2006 | White et al. |
| 2007/0088189 A1 | 4/2007 | Levy |
| 2007/0203429 A1 | 8/2007 | Ziv |
| 2007/0244352 A1 | 10/2007 | Ziv |
| 2008/0149109 A1 | 6/2008 | Ziv |
| 2008/0281149 A1 | 11/2008 | Sinai et al. |
| 2009/0266367 A1 | 10/2009 | Ziv et al. |
| 2009/0283099 A1 | 11/2009 | Harmanli |
| 2011/0065980 A1 | 3/2011 | Ziv et al. |
| 2012/0271098 A1 | 10/2012 | Ziv et al. |
| 2013/0165743 A1 | 6/2013 | Ziv et al. |

FOREIGN PATENT DOCUMENTS

| | | |
|---|---|---|
| EP | 0264258 | 4/1988 |
| EP | 0274762 | 7/1988 |
| EP | 0933069 | 8/1988 |
| EP | 0700669 | 3/1996 |
| EP | 0921778 | 6/1999 |
| EP | 0955024 | 11/1999 |
| EP | 1139963 | 10/2001 |
| EP | 1139962 | 5/2005 |
| EP | 1727491 | 12/2006 |
| FR | 2843700 | 2/2004 |
| GB | 1115727 | 5/1968 |
| GB | 2352181 | 1/2001 |
| GB | 2384436 | 7/2003 |
| JP | 63-177852 | 7/1988 |
| JP | 03-500489 | 2/1991 |
| JP | 06-133996 | 5/1994 |
| JP | 06-503982 | 5/1994 |
| JP | 61-33996 | 5/1994 |
| JP | 09-501595 | 2/1997 |
| JP | 2001-502929 | 3/2001 |
| JP | 2002-532198 | 2/2002 |
| JP | 2002-5332199 | 10/2002 |
| WO | WO 88/10106 | 12/1988 |
| WO | WO 89/09582 | 10/1989 |
| WO | WO 95/05790 | 3/1995 |
| WO | WO 96/01084 | 1/1996 |
| WO | WO 97/34550 | 9/1997 |
| WO | WO 98/49980 | 11/1998 |
| WO | WO 00/03659 | 1/2000 |
| WO | WO 00/36996 | 6/2000 |
| WO | WO 00/67662 | 11/2000 |
| WO | WO 02/26160 | 4/2002 |
| WO | WO 02/089704 | 11/2002 |
| WO | WO 03/047476 | 6/2003 |
| WO | WO 2004/000433 | 12/2003 |
| WO | WO 2004/103213 | 12/2004 |
| WO | WO 2005/087153 | 9/2005 |
| WO | WO 2005/087154 | 9/2005 |
| WO | WO 2006/097935 | 9/2006 |
| WO | WO 2008/010214 | 1/2008 |
| WO | WO 2008/079271 | 7/2008 |
| WO | WO 2008/152628 | 12/2008 |
| WO | WO 2009/044394 | 4/2009 |
| WO | WO 2009/130702 | 10/2009 |

OTHER PUBLICATIONS

Response Dated Oct. 11, 2011 to Decision for Rejection of Jun. 9, 2011 From the Japanese Patent Office Re. Application No. 2007-503495.

(56) References Cited

OTHER PUBLICATIONS

Examination Report Dated Oct. 13, 2010 From the Instituto Mexicano de la Propriedad Industrial Re. Application No. MX/a/2007/011339.
Examiner's Report Dated Dec. 15, 2010 From the Australian Government, IP Australia Re.: Application No. 2005221424.
Examiner's Report Dated Nov. 29, 2010 From the Australian Government, IP Australia Re. Application No. 2006224158.
Official Action Dated Dec. 28, 2010 From the US Patent and Trademark Office Re.: U.S. Appl. No. 10/593,367.
Response Dated Dec. 8, 2010 to Examiner's Report of Dec. 9, 2009 From the Australian Government, IP Australia Re.: Application No. 2005221424.
Response Dated Nov. 16, 2010 to Office Action of Sep. 17, 2010 From the State Intellectual Property Office of the People's Republic of China Re.: Application No. 200680017262.2.
Response Dated Oct. 20, 2010 to Official Action of Jun. 11, 2010 From the Federal Institute of Industrial and Intellectual Property, Patents and Trademarks, Rospatent, of the Russian Federation Re.: Application No. 2010100368.
Response Dated Sep. 30, 2010 to Communication Pursuant to Article 94(3) EPC of Mar. 23, 2010 From the European Patent Office Re.: Application No. 05718876.5.
Translation of Notification of Reasons for Rejection Dated Dec. 24, 2010 From the Japanese Patent Office Re. Application No. 2007-503495.
Translation of Office Action Dated Sep. 17, 2010 From the State Intellectual Property Office of the People's Republic of China Re.: Application No. 200680017262.2.
Communication Pursuant to Rules 70(2) and 70a(2) EPC and Reference to Rule 39(1) EPC Dated Jan. 9, 2012 From the European Patent Office Re. Application No. 11179593.6.
Response Dated Jan. 12, 2011 to Examination Report of Oct. 13, 2010 From the Instituto Mexicano de la Propriedad Industrial Re. Application No. MX/a/2007/011339.
Response Dated Jan. 13, 2011 to Official Action of Oct. 12, 2010 From the US Patent and Trademark Office Re.: U.S. Appl. No. 10/598,872.
Response Dated Jan. 17, 2011 to Examiner's Report of Dec. 15, 2010 From the Australian Government, IP Australia Re.: Application No. 2005221424.
Notice of Acceptance Dated Feb. 2, 2011 From the Australian Government, IP Australia Re.: Application No. 2005221424.
Examination Report Dated Jan. 16, 2012 From the Instituto Mexicano de la Propriedad Industrial Re. Application No. PA/a/2006/010653 and Its Summary in English.
Official Action Dated Feb. 15, 2012 From the US Patent and Trademark Office Re. U.S. Appl. No. 12/373,937.
Restriction Official Action Dated Feb. 28, 2012 From the US Patent and Trademark Office Re. U.S. Appl. No. 11/886,248.
Official Action Dated Feb. 9, 2011 From the US Patent and Trademark Office Re.: U.S. Appl. No. 10/593,367.
Communication Pursuant to Article 94(3) EPC Dated Feb. 4, 2011 From the European Patent Office Re. Application No. 04734069.0.
Communication Relating to the Results of the Partial International Search Dated Mar. 3, 2011 From the International Searching Authority Re. Application No. PCT/IL2010/000985.
Notification of Reasons for Rejection Dated Feb. 18, 2011 From the Japanese Patent Office Re. Application No. 2007-503494 and Its Translation into English.
Official Action Dated Feb. 14, 2011 From the US Patent and Trademark Office Re.: U.S. Appl. No. 10/598,872.
Request for Formal Examination Dated Feb. 24, 2011 From the ROSPATENT, Federal Government Institution, Federal Institute of Industrial Property of the Federal Service for Intellectual Property, Patents and Trademarks of the Russian Federation Re. Application No. 2010146714.
Examination Report Dated Feb. 16, 2012 From the Government of India, Patent Office, Intellectual Property Building Re. Application No. 3837/CBENP/2006.
Response Dated Mar. 28, 2011 to Official Action of Dec. 28, 2010 From the US Patent and Trademark Office Re.: U.S. Appl. No. 10/593,367.
Translation of Notification of Reasons for Rejection Dated Mar. 18, 2011 From the Japanese Patent Office Re. Application No. 2006-531002.
Translation of Office Action Dated Feb. 22, 2012 From the State Intellectual Property Office of the People's Republic of China Re. Application No. 200780033622.2.
Official Action Dated Apr. 9, 2012 From the US Patent and Trademark Office Re. U.S. Appl. No. 12/417,011.
Request for Examination Dated Mar. 29, 2012 From the Federal Institute of Industrial and Intellectual Property, Patents and Trademarks, ROSPATENT, of the Russian Federation Re. : Application No. 2010100368 and Its Summary in English.
Office Action Dated Apr. 5, 2011 From the Israel Patent Office Re.: Application No. 156070 and Its Translation Into English.
Response Dated Mar. 10, 2011 to Notification of Reasons for Rejection of Dec. 24, 2010 From the Japanese Patent Office Re. Application No. 2007503495.
Examination Report Dated Mar. 31, 2011 From the Instituto Mexicano de la Propriedad Industrial Re. Application No. MX/a/2007/011339.
International Search Report and the Written Opinion Dated May 9, 2011 From the International Searching Authority Re. Application No. PCT/IL2010/000985.
Translation of Office Action Dated Apr. 29, 2011 From the State Intellectual Property Office of the People's Republic of China Re.: Application No. 200680017262.2.
Requisition by the Examiner Dated May 22, 2012 From the Canadian Intellectual Property Office Re. Application No. 2,560,877.
Communication Under Rule 71(3) EPC Dated May 27, 2011 From the European Patent Office Re. Application No. 09735573.9.
Translation of Notification of Reasons of Rejection Dated Apr. 8, 2010 From the Japanese Patent Office Re.: Application No. 2007-503494.
Official Action Dated Apr. 29, 2010 From the US Patent and Trademark Office Re.: U.S. Appl. No. 10/598,872.
Supplemental Notice of Allowability Dated Apr. 27, 2010 From the US Patent and Trademark Office Re.: U.S. Appl. No. 10/557,865.
Communication Pursuant to Article 94(3) EPC Dated Mar. 23, 2010 From the European Patent Office Re.: Application No. 05718876.5.
Official Action Dated May 31, 2011 From the US Patent and Trademark Office Re. U.S. Appl. No. 12/417,011.
Translation of Decision for Rejection Dated Jun. 9, 2011 From the Japanese Patent Office Re. Application No. 2007-503495.
Translation of Notification of Reasons for Rejection Dated Jun. 1, 2010 From the Japanese Patent Office Re. Application No. 2006-531002.
Response Dated Jun. 21, 2010 to Office Action of Jan. 29, 2010 From the State Intellectual Property Office of the People's Republic of China Re.: Application No. 200680017262.2.
International Preliminary Report on Patentability Dated Jun. 7, 2012 From the International Bureau of WIPO Re. Application No. PCT/IL2010/000985.
Official Action Dated Jun. 23, 2010 From the US Patent and Trademark Office Re.: U.S. Appl. No. 10/593,367.
Second Supplemental Notice of Allowability Dated Jun. 3, 2010 From the US Patent and Trademark Office Re.: U.S. Appl. No. 10/557,865.
Response Dated Jun. 1, 2011 to Notification of Reasons for Rejection of Mar. 18, 2011 From the Japanese Patent Office Re. Application No. 2006-531002.
Response Dated Jun. 14, 2011 to Official Action of Feb. 14, 2011 From the US Patent and Trademark Office Re.: U.S. Appl. No. 10/598,872.
Response Dated May 29, 2011 to Communication Pursuant to Article 94(3) EPC of Feb. 4, 2011 From the European Patent Office Re. Application No. 04734069.0.
Response Dated Jun. 29, 2010 to Official Action of Apr. 29, 2010 From the US Patent and Trademark Office Re.: U.S. Appl. No. 10/598,872.

(56) References Cited

OTHER PUBLICATIONS

Official Action Dated Jun. 21, 2011 From the US Patent and Trademark Office Re.: U.S. Appl. No. 10/593,367.
Response Dated Jun. 20, 2011 to Office Action of Dec. 21, 2010 From the State Intellectual Property Office of the People's Republic of China Re. Application No. 200780033622.2.
Translation of Office Action Dated Dec. 21, 2010 From the State Intellectual Property Office of the People's Republic of China Re. Application No. 200780033622.2.
Official Action Dated Jun. 11, 2010 From the Federal Institute of Industrial and Intellectual Property, Patents and Trademarks, ROSPATENT, of the Russian Federation Re.: Application No. 2010100368 and Its Summary Into English.
Examination Report Dated May 30, 2012 From the Instituto Mexicano de la Propiedad Industrial Re. Application No. MX/a/2007/011339 and Its Translation Into English.
Response Dated Jun. 29, 2011 to Office Action of Apr. 29, 2011 From the State Intellectual Property Office of the People's Republic of China Re.: Application No. 200680017262.2.
Letter After Telephone Conference Dated Jul. 5, 2010 From the International Searching Authority Re. Application No. PCT/IL2009/000443.
Response Dated Jun. 5, 2011 to the Communication Pursuant to Article 94(3) EPC of Feb. 4, 2011 From the European Patent Office Re. Application No. 04734069.0.
Communiction Pursuant to Article 94(3) EPC Dated Jul. 2, 2010 From the European Patent Office Re.: Application No. 05718877.3.
International Preliminary Report on Patentability Dated Jul. 15, 2010 From the International Preliminary Examining Authority Re.: Application No. PCT/IL2009/000443.
Response Dated Aug. 7, 2011 to Office Action of Apr. 5, 2011 From the Israel Patent Office Re.: Application No. 156070.
Response Dated Aug. 10, 2011 to Official Action of May 31, 2011 From the US Patent and Trademark Office Re. U.S. Appl. No. 12/417,011.
Official Action Dated Jul. 23, 2012 From the US Patent and Trademark Office Re. U.S. Appl. No. 12/373,937.
Official Action Dated Aug. 4, 2010 From the US Patent and Trademark Office Re.: U.S. Appl. No. 10/598,872.
Response Dated Aug. 1, 2010 to Notification of Reasons of Rejection Dated Apr. 8, 2010 From the Japanese Patent Office Re.: Application No. 2007-503494.
Response Dated Aug. 11, 2011 to Examination Report of Mar. 31, 2011 From the Instituto Mexicano de la Propiedad Industrial Re. Application No. MX/a/2007/011339.
Patent Examination Report Dated Aug. 9, 2012 From the Australian Government, IP Australia Re. Application No. 2007274574.
Office Action Dated Jul. 24, 2011 From the Israel Patent Office Re. Application No. 176883 and Its Translation Into English.
Requisition by the Examiner Dated Aug. 22, 2012 From the Canadian Intellectual Property Office Re. Application No. 2,600,988.
Response Dated Aug. 30, 2010 to Notification of Reasons for Rejection of Jun. 1, 2010 From the Japanese Patent Office Re. Application No. 2006-531002.
Requisition by the Examiner Dated Aug. 29, 2011 From the Canadian Intellectual Property Office Re. Application No. 2,560,877.
Official Action Dated Aug. 24, 2012 From the US Patent and Trademark Office Re. U.S. Appl. No. 11/886,248.
Response Dated Aug. 31, 2010 to Official Action of Aug. 4, 2010 From the US Patent and Trademark Office Re.: U.S. Appl. No. 10/598,872.
Official Action Dated Oct. 14, 2011 From the US Patent and Trademark Office Re. U.S. Appl. No. 12/417,011.
Official Action Dated Oct. 12, 2010 From the US Patent and Trademark Office Re.: U.S. Appl. No. 10/598,872.
Response Dated Oct. 25, 2010 to Official Action of Jun. 23, 2010 From the US Patent and Trademark Office Re.: U.S. Appl. No. 10/593,367.
Reponse Dated Jun. 29, 2010 to Official Action of Apr. 29, 2010 From the US Patent and Trademark Office Re.: U.S. Appl. No. 10/598,872.

Translation of Office Action Dated Jan. 29, 2010 From the State Intellectual Property Office of the People's Republic of China Re.: Application No. 200680017262.2.
Communication Pursuant to Article 94(3) EPC Dated Nov. 3, 2011 From the European Patent Office Re. Application No. 07789949.0.
Response Dated Oct. 19, 2011 to Official Action of Jun. 21, 2011 From the US Patent and Trademark Office Re.: U.S. Appl. No. 10/593,367.
Response Dated Nov. 21, 2011 to Examiner's Report of Nov. 29, 2010 From the Australian Government, IP Australia Re. Application No. 2006224158.
Notice of Allowance Dated Nov. 14, 2011 From the US Patent and Trademark Office Re.: U.S. Appl. No. 10/593,367.
Examination Report Dated Oct. 13, 2011 From the Instituto Mexicano de la Propriedad Industrial Re. Application No. MX/a/2007/011339.
Examination Report Dated Oct. 13, 2010 From the Instituto Mexicano de la Propiedad Industrial Re. Application No. MX/a/2007/011339 and Its Summary in English.
Translation of Office Action Dated Nov. 22, 2012 From the State Intellectual Property Office of the People's Republic of China Re. Application No. 200780033622.2.
Translation of Search Report Dated Nov. 22, 2012 From the State Intellectual Property Office of the People's Republic of China Re. Application No. 200780033622.2.
Decision to Refuse a European Patent Application Dated Feb. 25, 2013 From the European Patent Office Re. Application No. 04734069.0.
Requisition by the Examiner Dated Feb. 19, 2013 From the Canadian Intellectual Property Office Re. Application No. 2,560,877.
Restriction Official Action Dated Feb. 6, 2013 From the US Patent and Trademark Office Re. U.S. Appl. No. 12/663,714.
Official Action Dated May 6, 2013 From the US Patent and Trademark Office Re. U.S. Appl. No. 11/886,248.
Supplemental Notice of Allowability Dated Apr. 2, 2013 From the US Patent and Trademark Office Re. U.S. Appl. No. 12/373,937.
Translation of Office Action Dated Mar. 5, 2013 From the State Intellectual Property Office of the People's Republic of China Re. Application No. 200980123856.5.
Translation of Reasons for Rejection Dated Mar. 18, 2013 From the Japanese Patent Office Re. Application No. 2011-223943.
Request for Examination Dated Apr. 4, 2013 From the Federal Service for Intellectual Property, Federal State Budgetary Institution, Federal Institute of Industrial Property of the Russian Federation Re. Application No. 2010146714 and Its Summary in English.
Requisition by the Examiner Dated May 28, 2013 From the Canadian Intellectual Property Office Re. Application No. 2,600,988.
Communication Pursuant to Rules 70(2) and 70a(2) EPC Dated Nov. 8, 2013 From the European Patent Office Re. Application No. 06711327.4.
Supplemental Notice of Allowability Dated Sep. 24, 2013 From the US Patent and Trademark Office Re. U.S. Appl. No. 11/886,248.
European Search Report and the European Search Opinion Dated Nov. 14, 2013 From the European Patent Office Re. Application No. 11188150.4.
Notice of Allowance Dated Jan. 7, 2013 From the US Patent and Trademark Office Re. U.S. Appl. No. 12/373,937.
Office Action Dated Dec. 5, 2012 From the Israel Patent Office Re. Application No. 176883 and Its Translation Into English.
Communication Pursuant to Article 94(3) EPC Dated Nov. 29, 2013 From the European Patent Office Re. Application No. 08808093.2.
Office Action Dated Nov. 12, 2013 From the State Intellectual Property Office of the People's Republic of China Re. Application No. 200980123856.5 and Its Translation into English.
Translation of Office Action Dated May 6, 2013 From the State Intellectual Property Office of the People's Republic of China Re. Application No. 200780033622.2.
Notice of Allowance Dated Oct. 2, 2013 From the US Patent and Trademark Office Re. U.S. Appl. No. 12/417,011.
Notification of Reasons for Rejection Dated Oct. 4, 2013 From the Japanese Patent Office Re. Application No. 2011-223943 and Its Translation Into English.

(56) References Cited

OTHER PUBLICATIONS

Official Action Dated Sep. 24, 2013 From the US Patent and Trademark Office Re. U.S. Appl. No. 13/772,410.
Supplementary European Search Report and the European Search Opinion Dated Oct. 21, 2013 From the European Patent Office Re. Application No. 06711327.4.
Translation of Office Action Dated Aug. 22, 2013 From the State Intelleetual Property Office of the People's Republic of China Re. Application No. 200780033622.2.
Invitation Pursuant to Rule 62a(1) EPC Dated Aug. 8, 2013 From the European Patent Office Re. Application No. 06711327.4.
Notice of Allowance Dated Aug. 6, 2013 From the US Patent and Trademark Office Re. U.S. Appl. No. 11/886,248.
Official Action Dated Jul. 1, 2013 From the US Patent and Trademark Office Re. U.S. Appl. No. 12/663,714.
Official Action Dated Jul. 23, 2013 From the US Patent and Trademark Office Re. U.S. Appl. No. 10/598,872.
Communication Pursuant to Article 94(3) EPC Dated Apr. 16, 2009 From the European Patent Office Re.: Application No. 05718876.5.
Communication Relating to the Results of the Partial International Search Dated Dec. 7, 2007 From the International Searching Authority Re.: Application No. PCT/IL2007/000893.
Communication Relating to the Results of the Partial International Search Dated Jan. 12, 2009 From the International Searching Authority Re.: Application No. PCT/IL2007/000893.
Communication Relating to the Results of the Partial International Search Dated Jan. 12, 2009 From the International Searching Authority Re.: Application No. PCT/IL2008/001292.
Communication Relating to the Results of the Partial International Search Dated Aug. 18, 2009 From the International Searching Authority Re.: Application No. PCT/IL2009/000443.
Communication Under Rule 112 EPC Dated Oct. 22, 2007 From the European Patent Office Re.: Application No. 05718876.5.
Communiction Pursuant to Article 94(3) EPC Dated Apr. 16, 2009 From the European Patent Office Re.: Application No. 05718877.3.
European Search Report Under Rule 112 EPC Dated Dec. 27, 2007 From the European Patent Office Re.: Application No. 05718876.5.
Examiner's Report Dated Dec. 9, 2009 From the Australian Government, IP Australia Re.: Application No. 2005221424.
International Preliminary Report on Patentability Dated Jul. 6, 2006 From the International Preliminary Examining Authority Re.: Application No. PCT/IL2005/000304.
International Preliminary Report on Patentability Dated Dec. 8, 2009 From the International Preliminary Examining Authority Re.: Application No. PCT/IL2008/001292.
International Preliminary Report on Patentability Dated Oct. 14, 2008 From the International Preliminary Examining Authority Re.: Application No. PCT/IL06/00346.
International Preliminary Report on Patentability Dated Dec. 23, 2009 From the International Bureau of WIPO Re.: Application No. PCT/IL2008/000786.
International Preliminary Report on Patentability Dated Jul. 24, 2006 From the International Preliminary Examining Authority Re.: Application No. PCT/IL2005/000303.
International Preliminary Report on Patentability Dated Jan. 29, 2009 From the International Bureau of WIPO Re.: Application No. PCT/IL2007/000893.
International Search Report and the Written Opinion Dated Oct. 26, 2005 From the International Searching Authority Re.: Application No. PCT/IL2005/000303.
International Search Report and the Written Opinion Dated Oct. 28, 2009 From the International Searching Authority Re.: Application No. PCT/IL2009/000443.
International Search Report Dated Dec. 11, 2006 From the International Searching Authority Re.: Application No. PCT/IL06/00346.
International Search Report Dated Apr. 14, 2008 From the International Searching Authority Re.: Application No. PCT/IL2007/000893.
International Search Report Dated Sep. 23, 2005 From the International Searching Authority Re.: Application No. PCT/IL2005/000304.
International Search Report Dated Oct. 24, 2008 From the International Searching Authority Re.: Application No. PCT/IL2008/000786.
International Search Report Dated Mar. 25, 2009 From the International Searching Authority Re.: Application No. PCT/IL2008/001292.
Notice of Allowance Dated Mar. 31, 2010 From the US Patent and Trademark Office Re.: U.S. Appl. No. 10/557,865.
Notification Dated Dec. 17, 2008 From the Patent Office of the Russian Federation Re.: Application No. 2006136791 and Its Translation into English.
Office Action Dated Sep. 1, 2008 From the Israeli Patent Office Re.: Application No. 156070 and Its Translation Into English.
Office Action Dated Sep. 1, 2008 From the Israeli Patent Office Re.: Application No. 157117 and Its Translation Into English.
Office Action Dated Jan. 9, 2009 From the State Intellectual Property Office of the People's Republic of China Re.: Application No. 200580016245.2 and Its Translation Into English.
Office Action Dated Jan. 18, 2010 From the Israel Patent Office Re.: Application No. 156070 and Its Translation Into English.
Official Action Dated Sep. 5, 2008 From the US Patent and Trademark Office Re.: U.S. Appl. No. 10/557,865.
Official Action Dated Mar. 6, 2009 From the US Patent and Trademark Office Re.: U.S. Appl. No. 10/557,865.
Official Action Dated Oct. 15, 2009 From the US Patent and Trademark Office Re.: U.S. Appl. No. 10/557,865.
Official Action Dated Apr. 17, 2009 From the Patent Office of the Russian Federation Re.: Application No. 2006136791 and Its Translation Into English.
Official Action Dated Feb. 19, 2010 From the US Patent and Trademark Office Re.: U.S. Appl. No. 10/593,367.
Official Action Dated Oct. 27, 2009 From the Federal Institute of Industrial and Intellectual Property, Patents and Trademarks, ROSPATENT, of the Russian Federation Re.: Application No. 2007138489 and Its Translation Into English.
Response Dated Mar. 15, 2010 to Official Action of Oct. 15, 2009 From the US Patent and Trademark Office Re.: U.S. Appl. No. 10/557,865.
Response Dated Feb. 22, 2010 to International Search Report and the Written Opinion of Oct. 28, 2009 From the International Searching Authority Re.: Application No. PCT/IL2009/000443.
Response Dated Mar. 25, 2010 to Official Action of Feb. 19, 2010 From the US Patent and Trademark Office Re.: U.S. Appl. No. 10/593,367.
Response Dated Dec. 27, 2009 to Official Action of Oct. 29, 2009 From the Federal Institute of Industrial and Intellectual Property, Patents and Trademarks, ROSPATENT, of the Russian Federation Re.: Application No. 2007138489.
Translation of Office Action Dated Jan. 19, 2010 From the State Intellectual Property Office of the People's Republic of China Re.: Application No. 200680017262.2.
Written Opinion Dated Dec. 11, 2006 From the International Searching Authority Re.: Application No. PCT/IL06/00346.
Written Opinion Dated Apr. 14, 2008 From the International Searching Authority Re.: Application No. PCT/IL2007/000893.
Written Opinion Dated Nov. 22, 2005 From the International Searching Authority Re.: Application No. PCT/IL2004/000433.
Written Opinion Dated May 23, 2006 From the International Preliminary Examining Authority Re.: Application No. PCT/IL2005/000303.
Written Opinion Dated Sep. 23, 2005 From the International Searching Authority Re.: Application No. PCT/IL2005/000304.
Written Opinion Dated Oct. 24, 2008 From the International Searching Authority Re.: Application No. PCT/IL2008/000786.
Written Opinion Dated Mar. 25, 2009 From the International Searching Authority Re.: Application No. PCT/IL2008/001292.

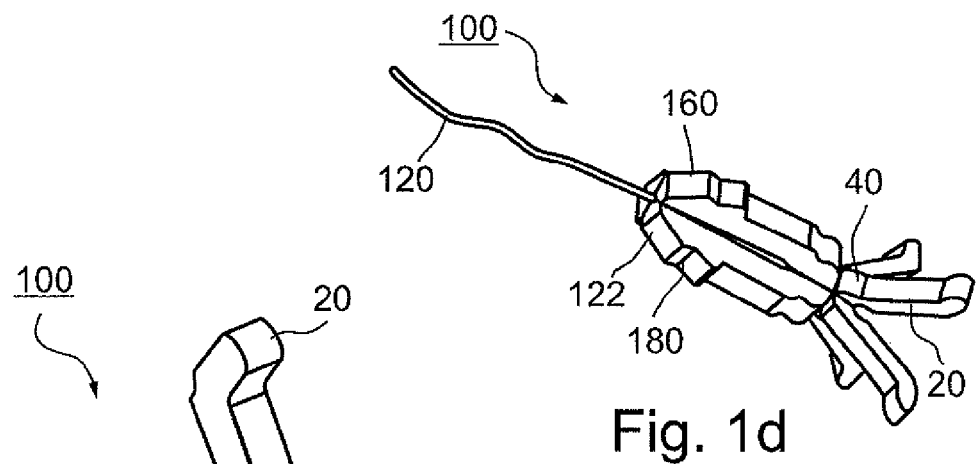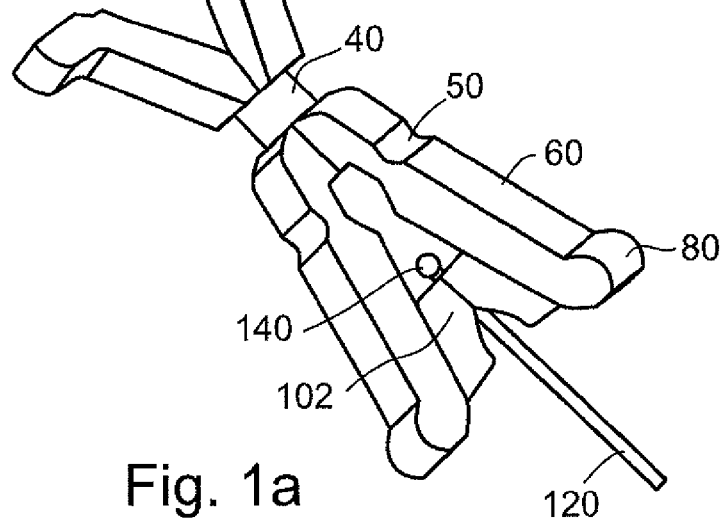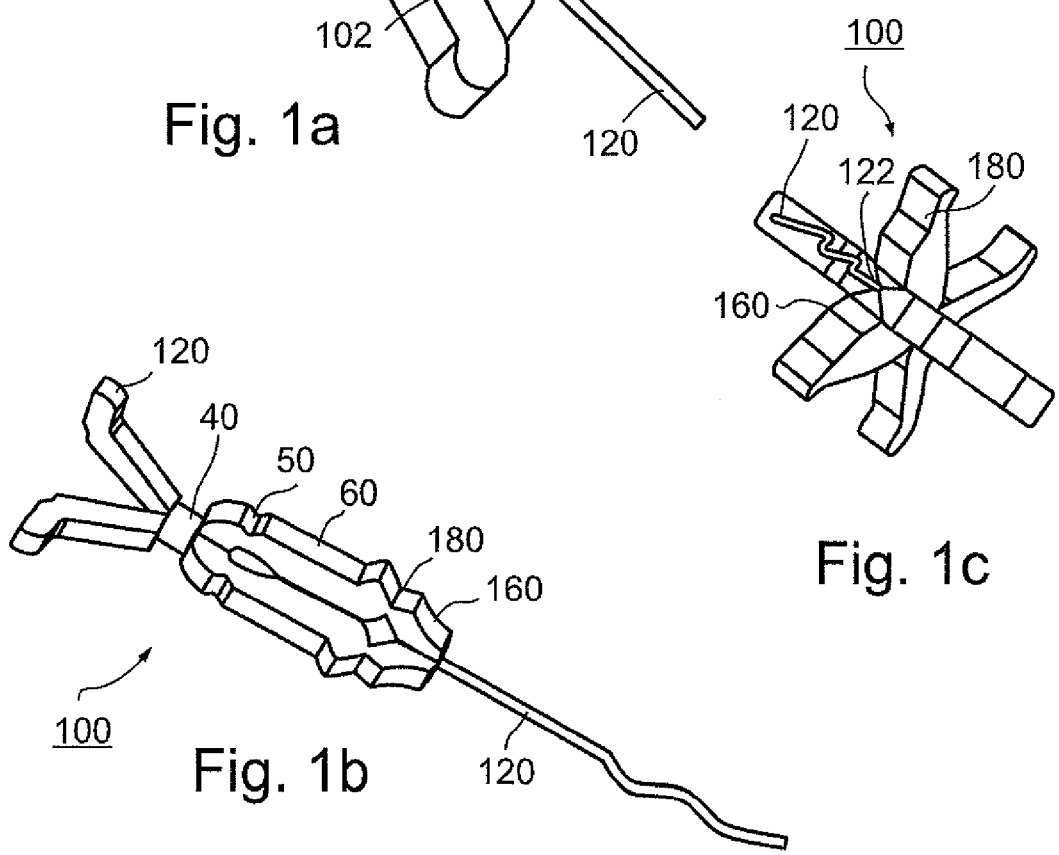

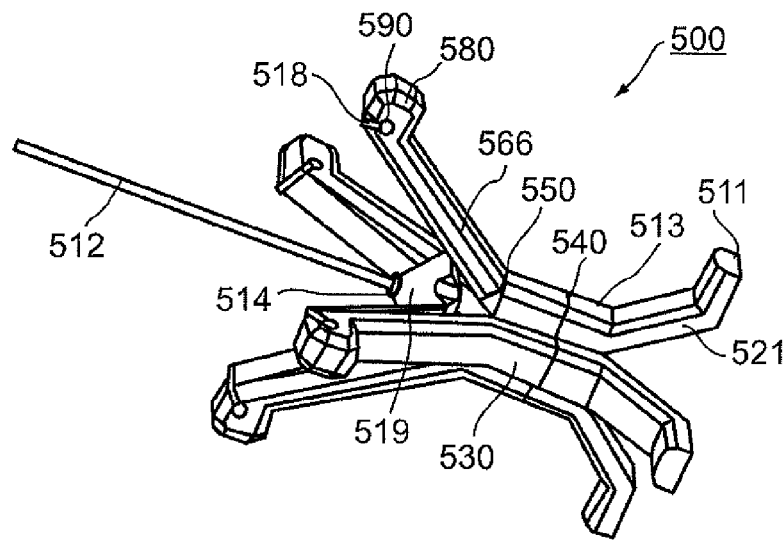
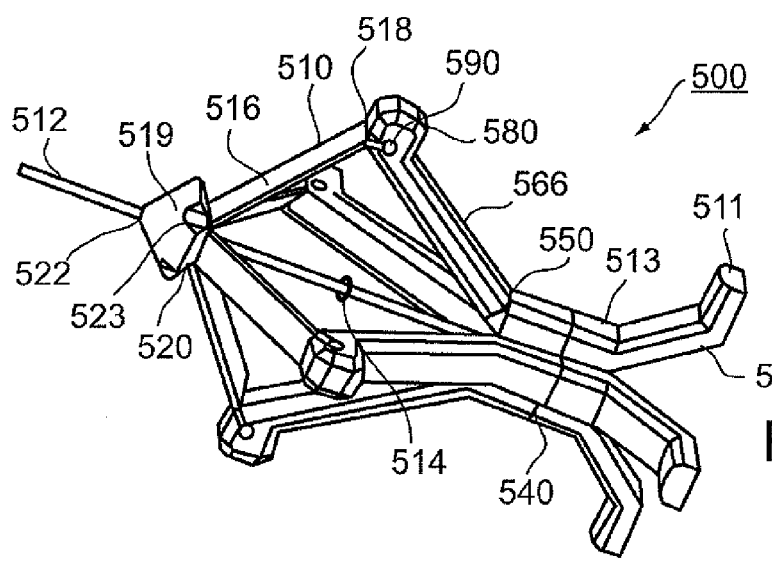
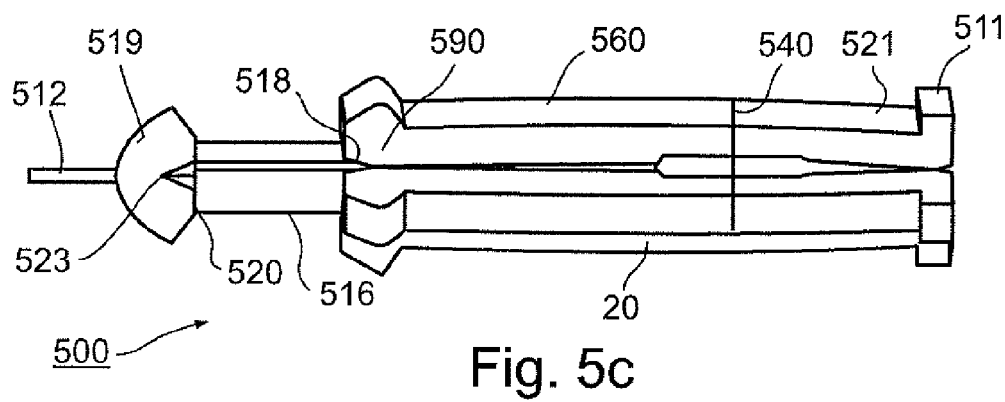

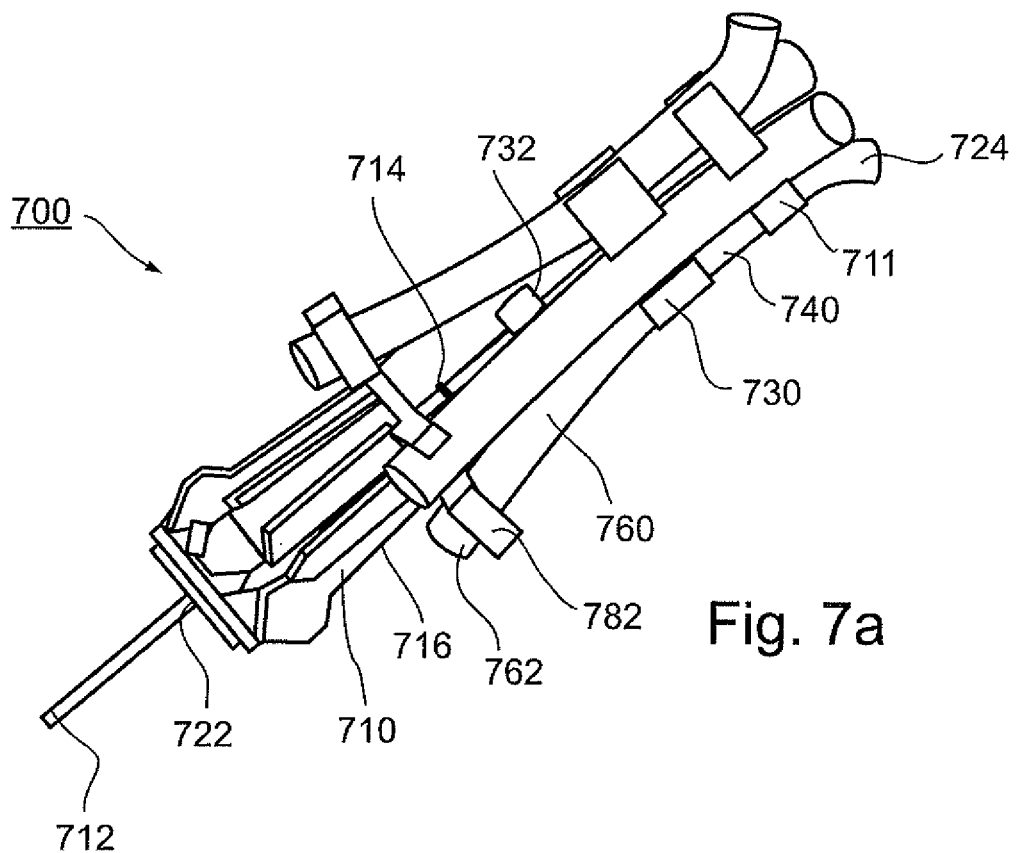
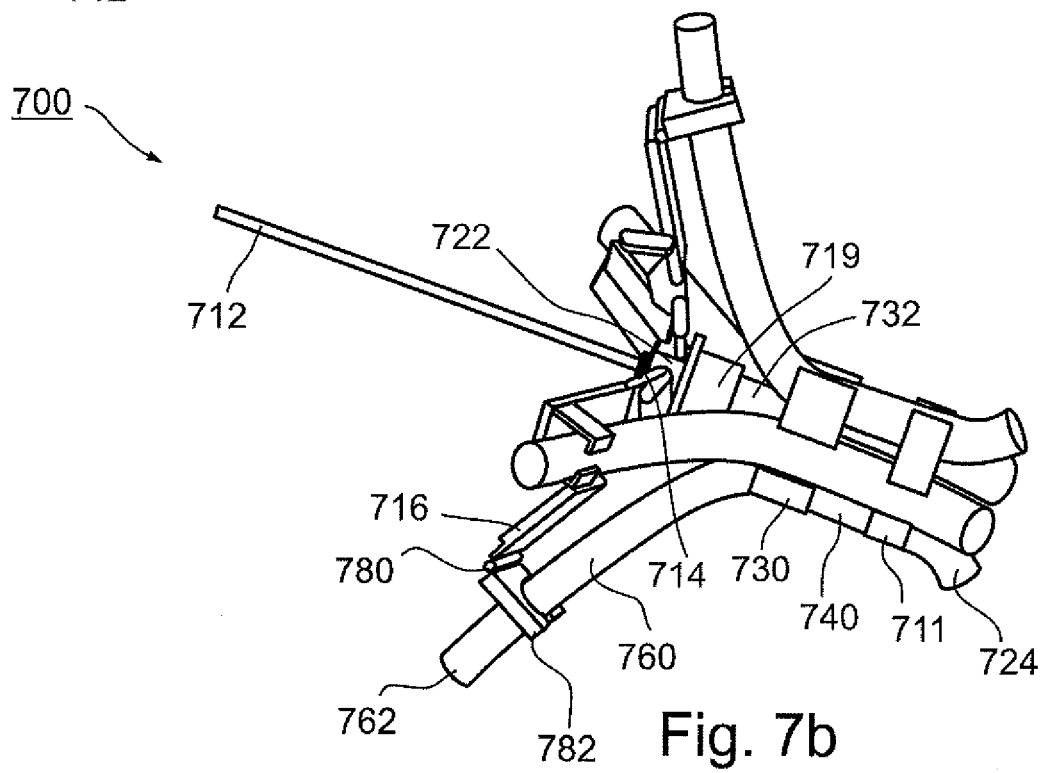

MANAGEMENT OF URINARY INCONTINENCE IN FEMALES

RELATED APPLICATIONS

The present application is a U.S. National Stage filing of PCT Application No. PCT/IL2008/001292 filed on Sep. 24, 2008.

The present invention also claims the benefit under 119(e) of U.S. provisional application Ser. No. 60/960,492, filed Oct. 1, 2007, the disclosures of which are incorporated herein by reference.

The teachings of related PCT Patent Applications Nos. PCT/IL2005/000304 filed on Mar. 17, 2005, PCT/IL2005/000303 filed Mar. 17, 2005, PCT/IL2004/000433 filed on May 20, 2004 and PCT/IL2006/000346 filed on Mar. 16, 2006, and U.S. Provisional Patent Application No. 60/762,059 filed on Jan. 25, 2006 are incorporated herein.

FIELD OF INVENTION

The present invention relates generally to treating feminine medical conditions, for example by providing devices for the prevention or amelioration of female incontinence.

BACKGROUND OF THE INVENTION

Urinary incontinence is a widespread problem among females. It is estimated that up to 50% of women occasionally leak urine involuntarily, and that approximately 25% of women will seek medical advice at some point in order to deal with the problem. Stress incontinence, the most common type of urinary incontinence, refers to the involuntary loss of urine resulting from abdominal pressure rise occurring during exercise, coughing, sneezing, laughing, etc. While many different factors may contribute to the development of stress incontinence, it is most prevalent among women ages 35-65 and those who have had multiple vaginal deliveries. Stress incontinence is both aggravating and unpleasant for women, and it can also be embarrassing. Many women wear sanitary pads or diapers in order to deal with incontinence, though this is not a real solution to the problem and it can be very inconvenient and unreliable. Surgical treatment may involve securing the paraurethal tissues to the periosteum of the pubic bone or the rectus facia in order to elevate the bladder neck above the pelvic floor and thereby distribute pressure equally to the bladder, the bladder neck, and the mid-urethra. Recently, a procedure known as "TVT" ("Tension Free Vaginal Tape") was developed, in which a mesh tape is implanted underneath the mid-urethra, creating a hammock on which the urethra may kink during a rise in intra-abdominal pressure. However, surgery is only suitable for severe cases, and the majority of women experiencing incontinence do not need, and certainly would rather avoid, surgical solutions.

One modality of non-surgical treatment involves the use of devices that are inserted into the vagina, either by a medical practitioner or by the woman herself. A variety of such devices are known in the art. For example, refer to U.S. Publication No. 2002/0183711 to Moser, entitled, "Urinary Incontinence Device"; U.S. Pat. No. 6,739,340 to Jensen, et al., entitled, "Device for prevention of involuntary urination"; U.S. Pat. No. 6,679,831 to Zunker, et al., entitled, "Resilient incontinence insert and a method of making the same"; U.S. Pat. No. 6,460,542 to James, entitled, "Female incontinence control device"; U.S. Pat. No. 6,413,206 to Biswas, entitled, "Intra-vaginal device"; U.S. Pat. No. 5,785,640 to Kresch, entitled "Method for Treating Female Incontinence"; U.S. Pat. No. 5,771,899 to Martelly, et al., entitled, "Pessary"; U.S. Pat. No. 5,618,256 to Reimer, entitled, "Device for Arrangement in the Vagina for Prevention of Involuntary Urination with Females and an Applicator for use in Insertion of the Device"; U.S. Pat. No. 5,417,226 to Juma, entitled, "Female Anti-Incontinence Device"; U.S. Pat. No. 5,386,836 to Biswas, entitled, "Urinary Incontinence Device"; U.S. Pat. No. 5,007,894 to Enhorning, entitled, "Female Incontinence Device"; and U.S. Pat. No. 4,920,986 to Biswas, entitled, "Urinary Incontinence Device", the disclosures of which are herein incorporated by reference.

SUMMARY OF THE INVENTION

An aspect of some embodiments of the invention relates to an intravaginal device for amelioration of incontinence including support arms which tend to open in a first operational state and have a second operational state in which the tendency to open is reduced. Optionally, opening is radially outwards with respect to a center axis of the device. Optionally, radial opening is up to 20% of the previous radial profile of the device. Optionally, radial opening is up to 50% of the previous radial profile of the device. In some embodiments, radial expansion is more than 50% of the previous radial profile of the device. Optionally, an increase in percentage of radial opening contributes to an ability of the device to ameliorate incontinence. In the open state, the device applies sufficient support underneath the urethra and/or surrounding tissues to inhibit a non-intentional flow of urine therethrough.

In an exemplary embodiment of the invention, an element which provides mechanical gain is used to control the radial profile and/or outwards force applied by the device. In an exemplary embodiment of the invention, the mechanical gain element, when applied, selectively causes the device to go from a large radius/force state to a low radius/force state and/or vice versa, when released. In an exemplary embodiment of the invention, the mechanical gain element is activated by axial force. Optionally, the axial force is selected so that a significant reduction in radial force/radius is achieved without sufficient axial force to cause digging in of the device into the vaginal walls.

The term "urethra" as used in this specification and the accompanying claims indicates any portion of the urethra including the bladder neck. In particular, some embodiments of the invention are configured to provide support to a mid-urethral region and some embodiments are configured to be located and/or operate when supporting a bladder neck portion of the urethra.

The phrase "normally open" as used in this specification and the accompanying claims indicates that opening occurs without a force applied from outside the apparatus. In an exemplary embodiment of the invention, a normally open expansion element of the device applies an opening force to the support arms at a distal portion thereof. Optionally, positioning of the expansion element distally with respect to the support arms contributes to a tendency of the device to be normally open.

Optionally, application of a deforming force to the normally open expansion element causes the support arms to become radially collapsed and/or axially extended. In an exemplary embodiment of the invention, upon removal of the deforming force, the expansion element automatically reverts to its normally open state.

Optionally, the expansion element comprises a plurality of components fitted together. Optionally, at least a portion of the expansion element is elastic (e.g. an elastic string or band). In some exemplary embodiments of the invention, the incontinence device is deployed using an applicator. Applicators suitable for use in the context of exemplary embodiments of the invention are described, for example, in WO 2005/087154; WO 2005/087153; WO 2004/103213 and WO 2006/097935 the disclosures of which are each fully incorporated herein by reference.

In an exemplary embodiment of the invention, the device comprises an adjustment mechanism (e.g. a string) adapted to allow a user to overcome an expansive force provided by the expansion element. In an exemplary embodiment of the invention, the adjustment mechanism, when activated, urges the device into the second operational state. Optionally, repositioning and/or removal of the device is done with the device in the second operational state.

In an exemplary embodiment of the invention, the adjustment mechanism contributes to easier and/or more comfortable removal from the vagina. Optionally, the adjustment mechanism causes radial components of the device to converge towards a midline (e.g. by pulling a string).

In an exemplary embodiment of the invention, the device is configured and/or positioned to provide mid-urethral and/or sub-urethral support. Optionally or alternatively, the device provides bladder neck support and/or raising. Such configuration may depend, for example, on the size and/or shape and/or orientation of a support section thereof and/or on a natural or possible anchoring place of the device in the vagina.

Optionally, the expansion element comprises a folding and/or hinged section. In an exemplary embodiment of the invention, folding and/or collapse of hinges contributes to an ability of the device to fit within an applicator which can be inserted into a vaginal opening without undue discomfort. According to these embodiments of the invention, upon deployment, the expansion element expands to extend the support arms outward to provide support and/or anchoring. Optionally, flexing of hinges in a first direction contributes to axial extension and radial collapse of the expansion mechanism while flexing of hinges in a second direction contributes to axial shortening and radial expansion of the expansion mechanism. In an exemplary embodiment of the invention, the flexing in the first direction reduces an overall diameter of the device and contributes to ease of vaginal insertion and/or storage in an applicator.

In some embodiments of the invention, an anchoring section provides resistance to axial motion and/or rotation. In some embodiments, resistance to axial motion in a direction opposite that provided by the anchoring section, is provided by the support section. In some embodiments, no separate anchoring section is provided.

An aspect of some exemplary embodiments of the invention relates to providing an incontinence device including portions characterized by different material properties in order to achieve a particular operational profile. In some exemplary embodiments of the invention, the support arms of the device comprise a first relatively flexible material, (e.g. silicon tubing) and the expansion element comprises a second relatively rigid material which provides support. Optionally, combination of two different materials contributes to a reduced overall device size and/or a longer shelf life. Optionally, combination of two different materials contributes to a reduction in tension of support arms during storage and/or a reduction in tension of the expansion element. In an exemplary embodiment of the invention, reduced tension during storage contributes to increased storage shelf life and/or reduced material fatigue.

In an exemplary embodiment of the invention, storage of the device in its second operational state contributes to a longer shelf life. Optionally, reduction of pressure on support arms during storage in an applicator contributes to increased shelf life. Optionally, support arms of exemplary devices according to embodiments of the invention are thinner and/or weaker than previously available alternatives. Optionally, reduced thickness and/or strength contribute to reduced production costs and/or device weight and/or device dimensions.

An aspect of some embodiments of the invention relates to assembly of an intravaginal device for amelioration of incontinence from a plurality of rods and at least one base adapted to connect the rods in a desired configuration. In an exemplary embodiment of the invention, the rods are constructed of a flexible material (e.g. silicon) and the base(s) are rigid. Optionally, assembly of rods and bases contributes to a reduction in production cost.

An aspect of some embodiments of the invention relates to rotational offset of anchor legs and support arms in an intravaginal device for amelioration of incontinence. Optionally, rotational offset contributes to reduced production cost and/or ease of removing a cast device from a production mold.

Optionally, the device is provided with a cover.

An aspect of some embodiments of the invention relates to control of a change in shape of the optional cover.

Optionally, collapse of the cover and the device are controlled by a single mechanism. In an exemplary embodiment of the invention, the single mechanism causes the cover to collapse after radial contraction and/or axial extension of the device have begun, optionally after they are complete.

Optionally, collapse of the cover and the device are controlled by separate mechanisms. In an exemplary embodiment of the invention, a first mechanism causes radial contraction and/or axial extension of the device and a second mechanism causes collapse of the cover (e.g. two different strings). In an exemplary embodiment of the invention, the second mechanism is operated after the first mechanism.

In an exemplary embodiment of the invention, the cover shape interacts with the device shape in a synergistic manner. In one example, the cover coordinates the collapse of various parts of the device. In another example, the cover conveys collapsing force to the support section of the device. In another example, the cover sets the expanded shape of the device by preventing expansion of some parts past the cover, while allowing the parts to apply significant force when slightly compressed inwards from the cover.

In an exemplary embodiment of the invention, the cover is porous to allow flow of vaginal discharges therethrough. Optionally or alternatively, the device is sparse, when viewed in an axial profile, to support flow of vaginal discharge therethrough.

An aspect of some embodiments of the invention relates to manufacturing an intravaginal device for amelioration of incontinence in a single piece. Optionally, the manufacturing is via injection molding. In an exemplary embodiment of the invention, the injection molding is in a mold with no undercuts.

There is provided in accordance with an exemplary embodiment of the invention, an apparatus for treating urinary incontinence, comprising:
(a) a support section adapted for providing at least one of urethral support and pressure against a portion of the urethra;
(b) an anchoring section adapted for resisting movement of said apparatus;
(c) a normally open expansion mechanism adapted to urge said support section radially outwards; and
(d) a conversion mechanism adapted to sharply and selectively reduce an outward urging of said support section.

Optionally, said support section comprises a plurality of support arms.

Optionally or alternatively, said support section is configured to provide urethra support.

In an exemplary embodiment of the invention, the expansion mechanism is adapted to urge without a force applied from outside the apparatus.

In an exemplary embodiment of the invention, the conversion mechanism is adapted to respond to a deforming force by axially extending, thereby causing radial collapse of the support arms. Optionally, the expansion mechanism is adapted to revert to the normally open state upon removal of the force.

In an exemplary embodiment of the invention, the expansion mechanism and the conversion mechanism are separate elements.

In an exemplary embodiment of the invention, said distal ends of said support arms apply sufficient force to vaginal walls to ameliorate incontinence.

In an exemplary embodiment of the invention, said conversion mechanism is adapted to urge said support arms radially inwards in response to a force applied from outside the apparatus. Optionally, the adjustment mechanism comprises a string attached to a hub of the expansion mechanism.

In an exemplary embodiment of the invention, the apparatus comprises:
a loading element connected to the expansion mechanism and adapted to urge at least a portion of the expansion mechanism axially towards said anchoring section. Optionally, the loading element comprises an elastic string adapted for attachment to a hub section of the expansion mechanism.

In an exemplary embodiment of the invention, said support arms are hinged.

In an exemplary embodiment of the invention, said support arms each comprise at lest two hinges.

In an exemplary embodiment of the invention, said support arms are flexible.

In an exemplary embodiment of the invention, urethral support is mid-urethral support.

In an exemplary embodiment of the invention, said expansion mechanism and said support section are integrally attached to one another. Optionally, said integral attachment to one another comprises integral hinges.

In an exemplary embodiment of the invention, said expansion mechanism and said support section comprise separate elements assembled to form the apparatus. Optionally, said expansion mechanism and said support section are connected by hinges.

In an exemplary embodiment of the invention, said apparatus is flexible.

In an exemplary embodiment of the invention, the expansion mechanism comprises elastic portions.

In an exemplary embodiment of the invention, the expansion mechanism comprises rigid portions.

In an exemplary embodiment of the invention, urethral support includes bladder neck support.

In an exemplary embodiment of the invention, the apparatus includes a cover.

In an exemplary embodiment of the invention, the apparatus comprises a cover collapse mechanism.

In an exemplary embodiment of the invention, said apparatus is rotationally symmetric.

In an exemplary embodiment of the invention, said apparatus is configured to operate independently of a rotational insertion angle.

In an exemplary embodiment of the invention, said apparatus is configured to allow passage of vaginal discharges therethrough when inserted.

There is also provided in accordance with an exemplary embodiment of the invention, a method for ameliorating urinary incontinence, the method comprising:
(a) intra-vaginally inserting an apparatus which provides at least one of support of pressure to a urethra, by a support section thereof;
(b) collapsing said support section after said insertion by application of force generally along an axis of said vagina;
(c) repositioning said apparatus by said axial force; and
(d) reducing said force to allow said support section to uncollapse and re-function as a support section.

Optionally, said collapsing comprises displacing a radially outwards urging element by said force.

Optionally or alternatively, said collapsing comprises displacing a rigidizing element by said force.

Optionally or alternatively, said collapsing comprises applying a greater axial force to start collapsing than to complete collapsing.

Optionally or alternatively, said collapsing comprises first increasing a radial extent of said support section as part of said collapsing.

Optionally or alternatively, the method comprises removing said apparatus using said force after (c).

Optionally or alternatively, inserting comprises inserting in a manner substantially oblivious to a rotational orientation of said apparatus.

There is also provided in accordance with an exemplary embodiment of the invention, an apparatus for treating urinary incontinence, comprising:
(a) an anchor section comprising a plurality of anchor legs; and
(b) a support section axially aligned with the anchor section and comprising a plurality of support arms;
wherein no anchor leg is in direct axial alignment with a support arm.

Optionally, a number of anchor legs is equivalent to a number of support arms. There is also provided in accordance with an exemplary embodiment of the invention, an apparatus for treating urinary incontinence, comprising:
(a) an anchor section comprising a plurality of anchor legs and an anchor connector; and
(b) a support section comprising a plurality of support arms and a support connector;
wherein the anchor connector and support connector are adapted for connection one to another.

Optionally, connection of the anchor connector and support connector one to another fixes an axial alignment of the anchor legs and support arms.

Optionally or alternatively, connection of the anchor connector and support connector one establishes a rotating joint between the anchor section and the support section.

There is also provided in accordance with an exemplary embodiment of the invention, an apparatus for treating urinary incontinence, comprising:
(a) a plurality of rods, each rod characterized by a proximal section, a midsection and a distal section;
(b) at least one base, the at least one base adapted to engage and retain each rod; and
(c) an expansion mechanism comprising a hub and a spoke for each rod, each spoke adapted at a distal end thereof to engage and retain a distal section of a rod.

Optionally, the hub of the expansion mechanism is adapted to contact a neck of the at least one base.

Optionally or alternatively, the at least one base comprises an anchor base and a support base adapted to engage and retain each rod at the proximal section and the midsection respectively. Optionally, the hub is adapted to contact a neck of the support base.

Optionally or alternatively, the expansion mechanism is normally open so that the spokes extend the distal sections of the rods radially outwards with respect to central axis passing through the at least one base.

In an exemplary embodiment of the invention, the rods are formed of tubing.

In an exemplary embodiment of the invention, the hub engages the neck.

BRIEF DESCRIPTION OF THE FIGURES

Non-limiting embodiments of the invention will be described with reference to the following description of exemplary embodiments, in conjunction with the Figures. The Figures are generally not shown to scale and any measurements are only meant to be exemplary and not necessarily limiting. In the Figures, identical structures, elements or parts which appear in more than one Figure are preferably labeled with a same or similar number in all the Figures in which they appear, in which:

FIG. 1a is a perspective view of an exemplary device according to one embodiment of the invention in its normally open state;

FIGS. 1b and 1d are perspective views of the exemplary device of FIG. 1a, closed or collapsed in similar and opposite orientations as FIG. 1a;

FIG. 1c is perspective view of the exemplary device of FIG. 1a in its normally open state inverted to the orientation of FIG. 1d so that the exemplary expansion element is more clearly visible;

FIG. 2b is a side view of the device of FIG. 2a;

FIG. 3b is isometric side view the exemplary device of FIG. 3a;

FIG. 3d is perspective view of a support arm and corresponding portion of the expansion element removed from the device of FIG. 3a;

FIG. 4c is a bottom view of the device of FIG. 4a;

FIG. 5a is a perspective view of an exemplary device according to another exemplary embodiment of the invention in its normally open position;

FIG. 5b is a perspective view of the exemplary device of the device of FIG. 5a in an intermediate state between an open position and a collapsed position;

FIG. 5c is a side view of the exemplary device of the device of FIG. 5a in a collapsed position achieved by application of an external force;

FIG. 7a is a perspective view of an exemplary device according to another exemplary embodiment of the invention in a collapsed state achieved by application of an external force;

FIG. 7b is a side view of the device of FIG. 7a in its normally open position;

DETAILED DESCRIPTION OF EXEMPLARY EMBODIMENTS

Overview

Figure 1E:
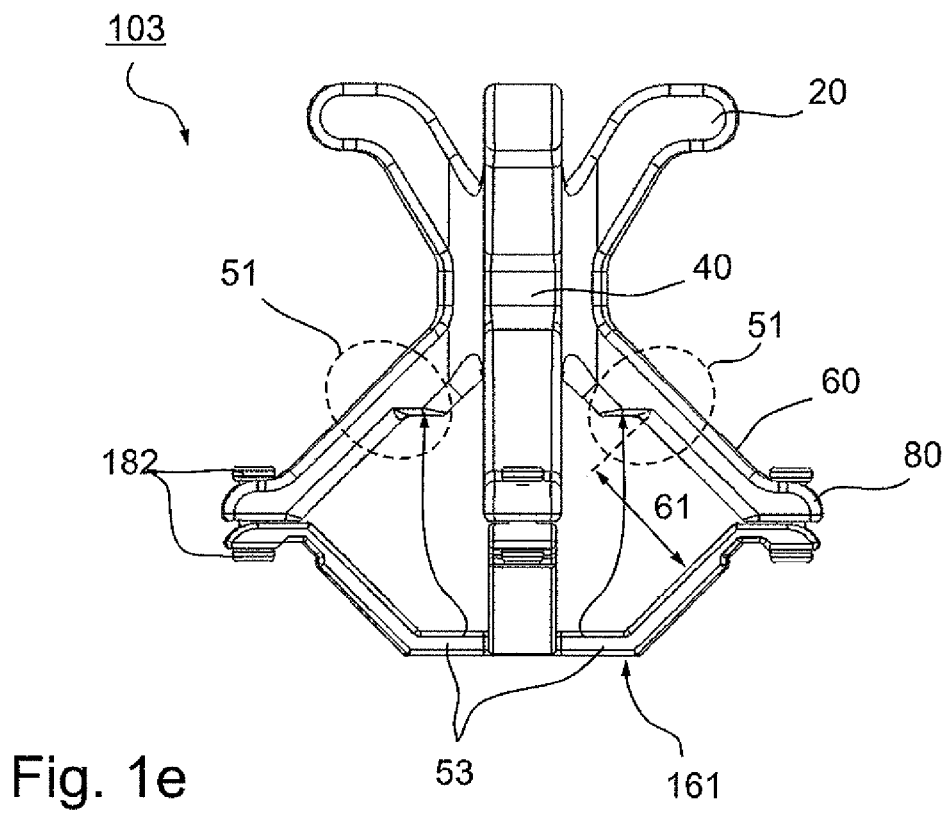
FIG. 1e is a side view of an additional exemplary device according to another embodiment of the invention closed or collapsed as in FIG. 1b.

Previous international patent applications WO 2005/087154; WO 2004/103213 and WO 2006/097935, which all have at least one inventor in common with the instant application, each describe vaginally implantable devices for the control of incontinence. Each of these earlier applications is fully incorporated herein by reference. Many of the devices described in these earlier applications include an anchor section, optionally comprising anchor legs, and a supporting section, optionally comprising one or more support arms.

In an exemplary embodiment of the invention, the normally open expansion mechanism of exemplary devices described herein urges distal ends of support arms radially outwards. In embodiments described herein, the urging occurs without a force applied from outside the apparatus, or as a result of a force transiently applied to a loading mechanism. Optionally, an axial length of a device according to exemplary embodiments of the invention is between 30 mm and 70 mm in its normally open state. In an exemplary embodiment of the invention, collapse of the device (e.g. during storage in an applicator) can increase device length by as little as 0 mm or as much as 30 mm and/or shorten the device.

In an exemplary embodiment of the invention, a conversion element is provided which, when activated, sharply reduces the radial outwards urging, easing removal and/or repositioning of the device. In an exemplary embodiment of the invention, the conversion element provides a mechanical gain, so that an axial force used to activate the conversion element is significantly smaller than the reduction in radial force and/or is sufficient to reduce or prevent digging in of the support section in vaginal walls due to axial force conveyed to the device by the conversion element.

Exemplary Contiguously Formed Normally Open Expansion Elements

Hinged Arcs

FIG. 1a is perspective view of an exemplary device 100 according to one embodiment of the invention in its normally open state. In the depicted embodiment, device 100 includes an anchor section comprising a plurality of anchor legs 20. Four anchor legs 20 are depicted although various embodiments of the device can have any number of anchor legs (e.g. 1, 2, 3, 6 or 8). Optionally, narrowed portions 50 of support arms 60 contribute to flexibility of support arms 60 during collapse of the device (e.g. for insertion in an applicator) and the convergence towards the midline when expansion element is axially extended with respect to the device.

Device 100 also comprises a support section including a plurality of support arms 60 ending in "hands" 80. Four support arms 60 are depicted although various embodiments of the device can have any number of support arms. In an exemplary embodiment of the invention, four hands 80 contribute to increased conformity with para-urethral anatomy adjacent to the anterior wall of the vagina. Optionally, hands 80 arrange themselves inside the vaginal recesses on both sides of the urethra.

In an exemplary embodiment of the invention, extension element 102 is deployed between arms 60 and is connected to, or near, distal hands 80. Optionally, connection of extension element 102 at or near hands 80 contributes to an increase in expansion capability. In the depicted embodiment, extension element 102 comprises four arcuate elements 160 (seen in FIGS. 1b; 1c and 1d). Optionally, each of arcuate elements 160 is connected to or near one of hands 80 by an integral hinge 180. Optionally, arcuate elements 160 converge at a hinged or flexible hub 122.

In the depicted embodiment, anchor legs 20 are connected to arms 60 by a transition neck 40. In an exemplary embodiment of the invention, transition neck 40 is flexible and/or permits rotation of legs 20 with respect to arms 80. Optionally, legs 20 are manufactured separately from arms 80 and neck 40 comprises two interconnecting pieces. Optionally legs 20 may be manufactured of a different material. Legs 20 may rotate to any direction away from the axis of the device due to the flexibility of neck 40.

In an exemplary embodiment of the invention, device 100 has two operational states. FIGS. 1a and 1c depict device 100 in its normally open state. In the normally open state, extension element 102 assumes a bowl-like shape between arms 60 and extends hands 80 radially outwards. In this operational state, device 100 can provide urethral support when placed in the vagina.

In the depicted embodiment, the configuration of FIGS. 1a and 1c is stable and the device tends to revert to this configuration from the axially extended configuration of FIGS. 1b and 1d. Optionally, the design of a mold used to produce device 100 causes expansion element 102 to automatically revert to a stable position between the arms 80. Optionally, expansion element 102 assists in keeping arms 60 open, or may be the reason why these arms are kept open, when the arms are designed to be weak and/or constructed of material with a low shore hardness.

In the depicted embodiment, device 100 is equipped with an adjustment mechanism in the form of a string 120 attached to an anchor 140 at hub 122 of expansion element 102. Pulling on string 120 causes hub 122 to evert around flex hinges 180 so that device 100 assumes its closed operational state as seen in FIGS. 1b and 1d. The depicted exemplary geometry causes thin areas 50 to flex (see FIG. 1b). Optionally, this flexing contributes to a reduction in overall device diameter.

In the depicted embodiment, the closed operational state is unstable in the absence of an externally applied force. Arms 60 collapse inwards in the closed operational state so that an external diameter of the device is reduced. The reduced external diameter is useful for storage (e.g. in an applicator) and/or intra-vaginal adjustment and/or removal of device 100. In an exemplary embodiment of the invention, when tension on string 120 is released, device 100 returns to the normally open state of FIGS. 1a and 1c. In an exemplary embodiment of the invention, return to the normally open state results from an inherent elasticity of arms 60 and/or expansion element 102, or both. Optionally, flex points 50 contribute to this flexibility. In an exemplary embodiment of the invention, an amount of radial contraction force needed to maintain device 100 in the closed state of FIGS. 1b and 1d is low. Optionally, this radial contraction force is provided by an axial translation of string 120 and translated to radial contraction by hub 122 and expansion element 102.

Device 100 can be produced using known commercial processes such as, for example, injection molding. In an exemplary embodiment of the invention, device 100 is cast as a single piece or as separate pieces in a two or four part mold. Optionally, division between mold parts is longitudinal and/or latitudinal. Molded parts can be assembled by gluing, snapping, matching threaded parts, welding or any other known connection strategy.

In an exemplary embodiment of the invention, division between molded pieces is horizontal at the level of the flexible neck 40. Optionally, anchoring legs 20 and support arms 60 are assembled by snapping together mated parts of neck 40.

FIG. 1e is a side view of an additional exemplary device 103 according to another embodiment of the invention closed or collapsed as in FIG. 1b. Device 103 operates in a manner similar to that described hereinabove for device 100. In the depicted embodiment, expansion mechanism 161 is manufactured separately and attached to support arms 60 at hands 80 by connectors 182. Connectors 182 may be, for example, threaded bolts (optionally with matching nuts, screws, rivets, grommets, cotter pins or similar). In an exemplary embodiment of the invention, separate assembly of expansion mechanism 161 contributes to ease of achieving different flexibility of the expansion mechanism and support arms 60.

In the depicted embodiment, as the device returns to its normally open state (similar to FIG. 1a), expansion mechanism 161 moves axially towards neck 40 so that horizontal bars 53 come to rest against steps 51 of support arms 60. Alternatively, or additionally, presence of steps 51 in support arms 60 contributes to arm flexibility by creating narrowed portions 61.

Straight Bars

Figure 2A:
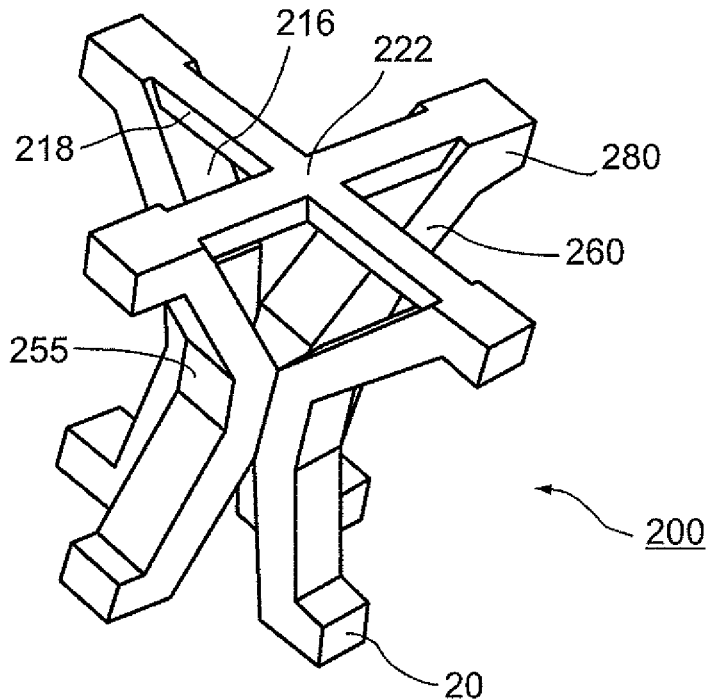
FIG. 2a is a perspective view of an additional exemplary device according to another embodiment of the invention in its normally open state.
Figure 2B:
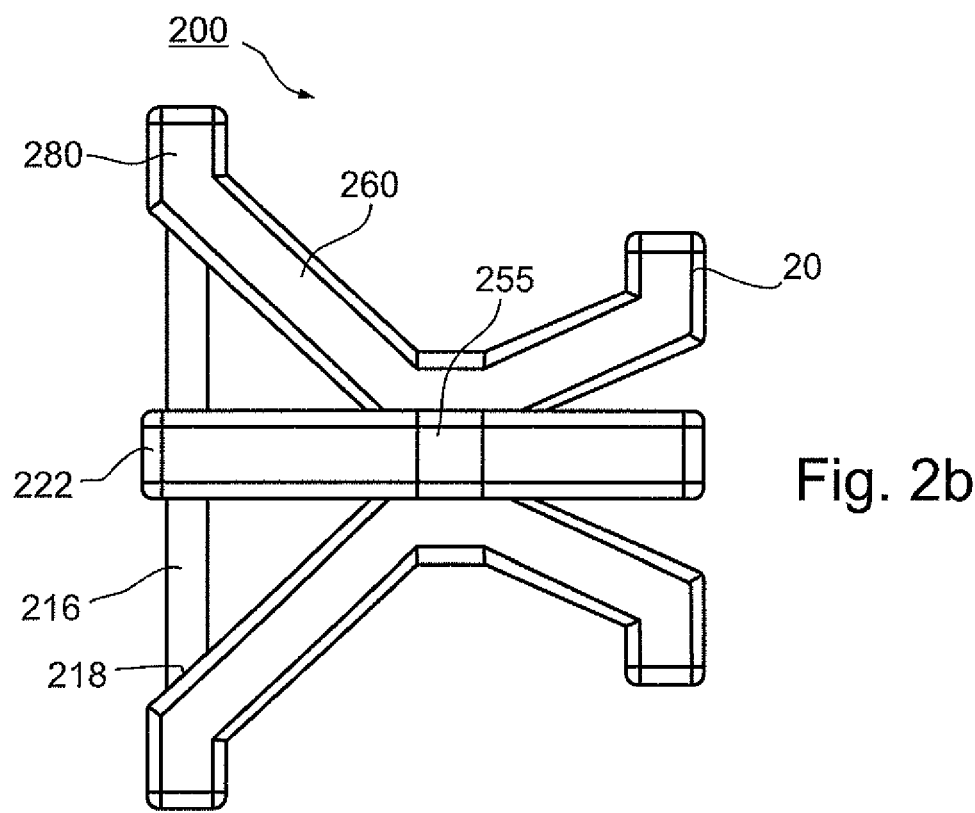

FIG. 2a is a perspective view of an additional exemplary device 200 according to another embodiment of the invention in its normally open state. FIG. 2b is a side view of the device of FIG. 2a.

In depicted exemplary device 200, the arcuate elements 160 of the expansion element are replaced by bars 216 connecting each of hands 280 of support arms 260 to a hinged hub 222. Additional integral hinges 218 are deployed between hands 280 of arms 260 and bars 216. In the depicted exemplary embodiment, neck 255 between anchoring legs 20 and support arms 260 is flexible.

Transition to the closed operational state is via an adjustment mechanism (not shown), for example a string as described above for device 100.

Device 200, like device 100, assumes the depicted open operational state in which bars 216 expand hands 280 radially outwards in the absence of an input force applied though the adjustment mechanism. Depicted bars 216 provide a large amount of radial support when open but do not resist folding to an unacceptable degree. In physiologic stress situations (e.g. a cough or sneeze), resistance to folding is sufficiently high that support is not compromised and incontinence is avoided. In manipulation situations (e.g. repositioning or removal) resistance to folding is sufficiently low that it is easily overcome by manual manipulation. In an exemplary embodiment of the invention, manual manipulation is implemented by a string (not shown) connected to hub 222. Optionally, when the string is pulled, hub 222 extends axially away from neck 255 causing hands 280 to converge radially inwards. In an exemplary embodiment of the invention, the convergence causes a reduction in overall device diameter which can contribute to ease of repositioning and/or removal.

Integral Arcs

Figure 3A:
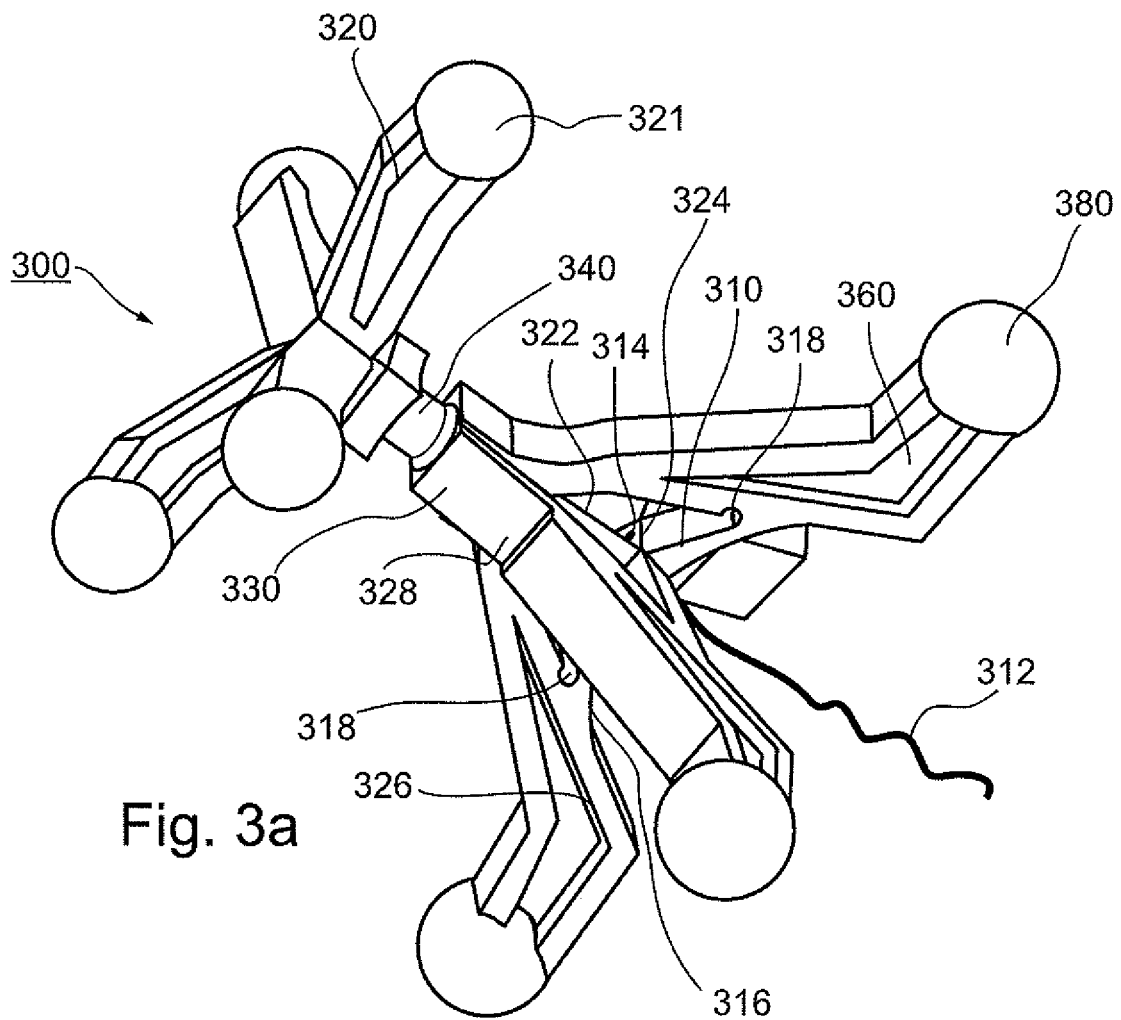
FIG. 3a is perspective view of another exemplary device according to one embodiment of the invention in its normally open state.
Figure 3B:
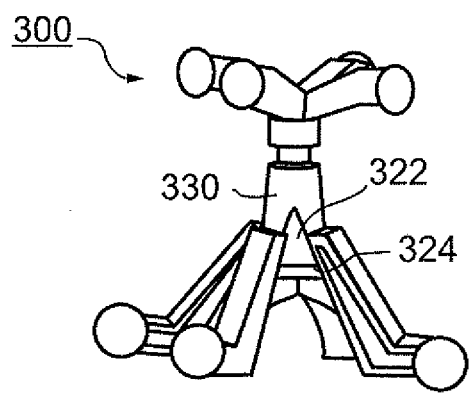
Figure 3C:
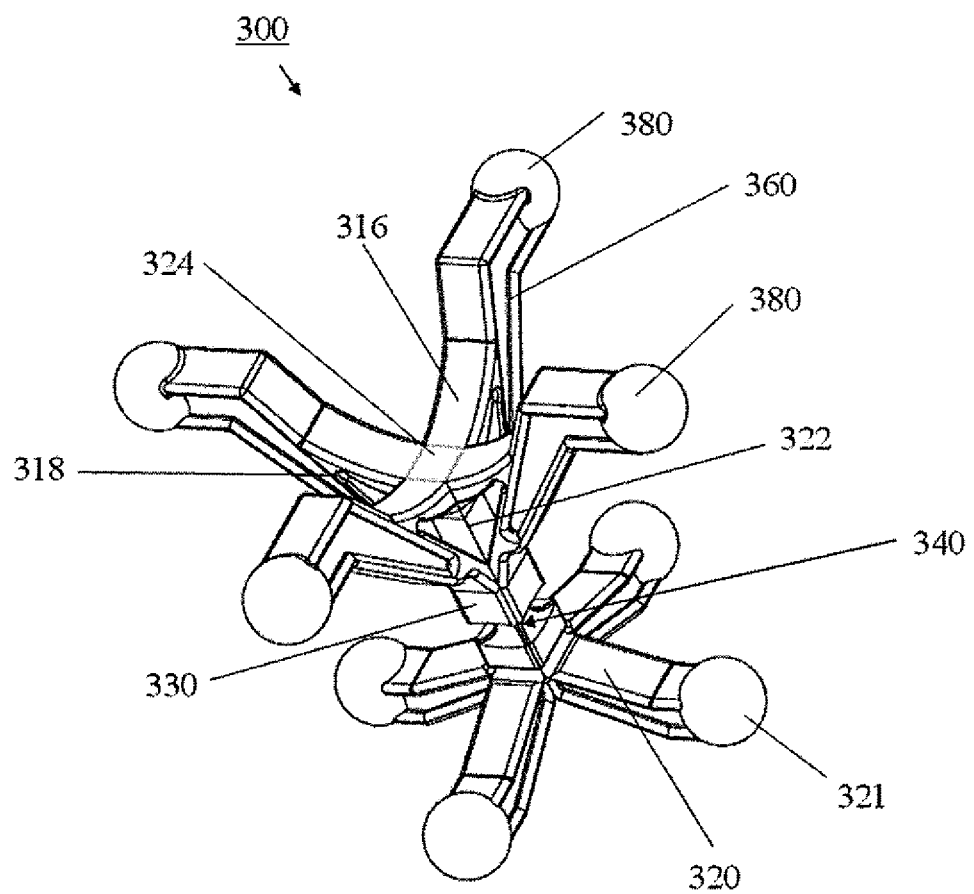
FIG. 3c is an isometric bottom view of the exemplary device of FIG. 3a depicting the expansion element clearly.
Figure 3D:
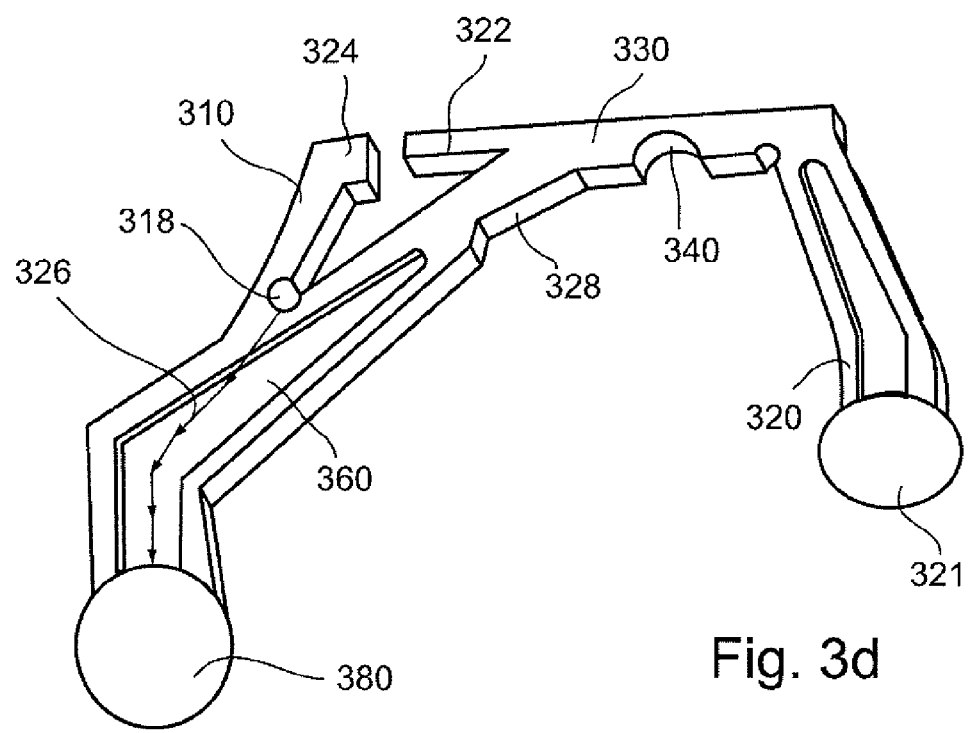
Figure 3E:
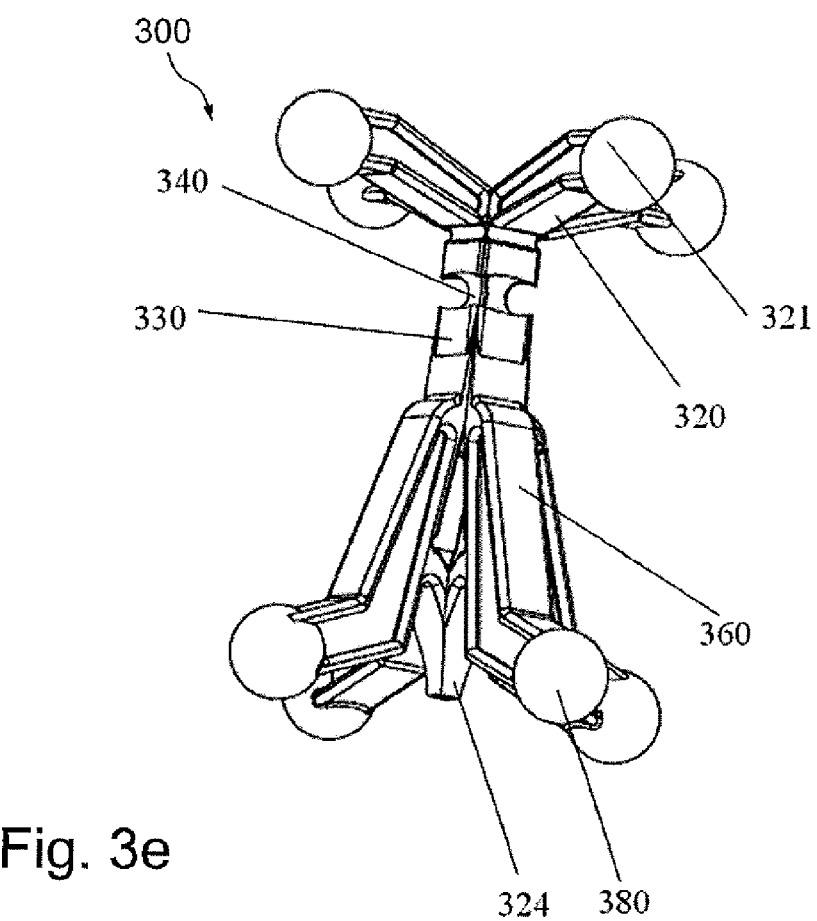
FIG. 3e depicts the exemplary device of FIG. 3a in a collapsed state.

FIG. 3a is perspective view of another exemplary device 300 according to one embodiment of the invention in its normally open state. FIG. 3b is a side view of exemplary device 300 and FIG. 3c is a bottom view of device 300 depicting the expansion element 310 more clearly. FIG. 3d is a perspective view of a support arm and corresponding portion of expansion element 310 removed from device 300. FIG. 3e depicts a similar device in a radialy convergent axially extended position.

In an exemplary embodiment of the invention, expansion element 310 comprises four arcs 316 which are an integral part of device 300.

Exemplary device 300 comprises an anchoring portion with four anchor legs 320 each terminating in a shoe 321.

In the depicted embodiment, a flexible neck 340 connects the anchor portion to a support portion comprising a wider body 330 and four support arms 360 each terminating in a ball shaped hand 380. Optionally, a ball shaped hand 380 provides more surface contact with body tissues and can contribute to reduced mucosal insult.

In the depicted embodiment, expansion element 310 comprises four arcs 316. Each arc 316 is flexibly connected to corresponding support arm 360 by a slit like hinge 318 (FIG. 3d) at one end, and to an opposite arc 316 at flexible hub 324. Optionally, a length of the arcs may be manipulated by positioning of hinge 318 along a path depicted by arrows 326. Optionally, positioning of hinge 318 closer to hand 380 contributes to an increase in flexibility of support arm 360.

FIG. 3d illustrates that the distance from hub 324 to hinge 318 defined by expansion element 310 allows for movement and/or for some flexibility. As this distance increases (depicted by arrow line 326), outward movement of expansion mechanism 310 is easier due to increased flexibility.

During exemplary use, (e.g. repositioning or removal) a pull string 312 (FIG. 3a) contributes to axial extension of hub 324 towards a plane occupied by hands 380. This axial extension contributes, in turn to radial convergence of hands 380 of device 300 as depicted in FIG. 3e.

In the depicted embodiment, an adjustment mechanism in the form of a string 312 connected to an anchor 314 at flexible hub 324 is provided. The adjustment mechanisms functions as described above for device 100.

In an exemplary embodiment of the invention, hinges 318 are positioned close to hands 380 to make expansion mechanism 310 softer. Optionally, a softer expansion mechanism contributes to a reduction in forces needed to collapse the device.

Operation of the adjustment mechanism by pulling on the string causes expansion element 310 to invert from the normally open position within the arms depicted in FIG. 3a to a closed position outside support arms 360 (FIG. 3e). Inversion of arcs 316 is possible due to the hinges 318 and 324 as described hereinabove. When string 312 is pulled, expansion element 310 moves into a second position outside support arms 360 and arms 360 collapse and converge towards a midline of device 300. Thinning of the proximal part of the arms 328 optionally acts as a hinge which contributes to a reduction in resistance to the collapse. Collapse of device 300 allows prolonged storage within an applicator and/or comfortable insertion and/or removal from the vagina.

A degree of outwards extension of expansion element 310 can vary with relative position of hinges 318 with respect to support arms 360 along line 326.

In an exemplary embodiment of the invention, when the extension mechanism 310 is in the depicted normally open position between support arms 360, hands 380 produce a predefined force influenced by arms 360 and a degree of overall flexibility of the device. Optionally, limiting element 322 limits inward movement of hub 324 towards neck 340. In an exemplary embodiment of the invention, device dimensions are selected in consideration of a size of a particular patient. Optionally, devices are available in 2, 3 or 4 sizes (e.g., small, medium, large).

If the vagina is too wide relative to the device, arms 360 may contact the inner vaginal wall or may contact with insufficient force to provide desired support.

Optionally, a force applied to the vaginal wall by the device can be controlled by adjusting device dimensions and/or flexibility. In an exemplary embodiment of the invention, the device is designed so that the four hands lie on a curve with predefined dimensions (e.g. circle with predefined diameter) when the device is in the normally open state of FIG. 3a.

In an exemplary embodiment of the invention, a degree of inward flexibility of the expansion element 310 is determined by limiting element 322 on body 330 and hub 324 joining the four arcs 316. Optionally, flexibility and/or outward forces generated by hands 380 can be limited to a desired degree by adjusting a length of limiting element 322 on body 330 and/or a height of hub 324 joining the four arcs 316.

Exemplary Continuous Support Arm/extension Element

Figure 4A:
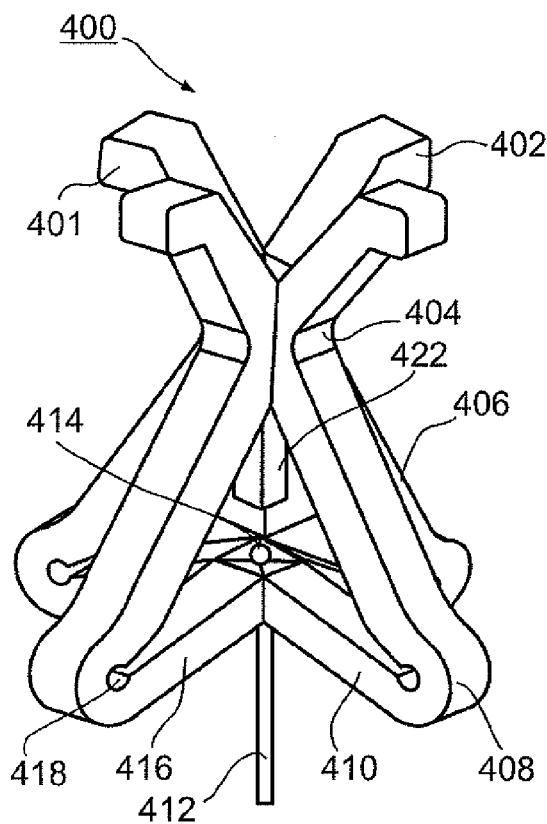
FIG. 4a is a side view of an exemplary device according to another embodiment of the invention in its normally open position.
Figure 4B:
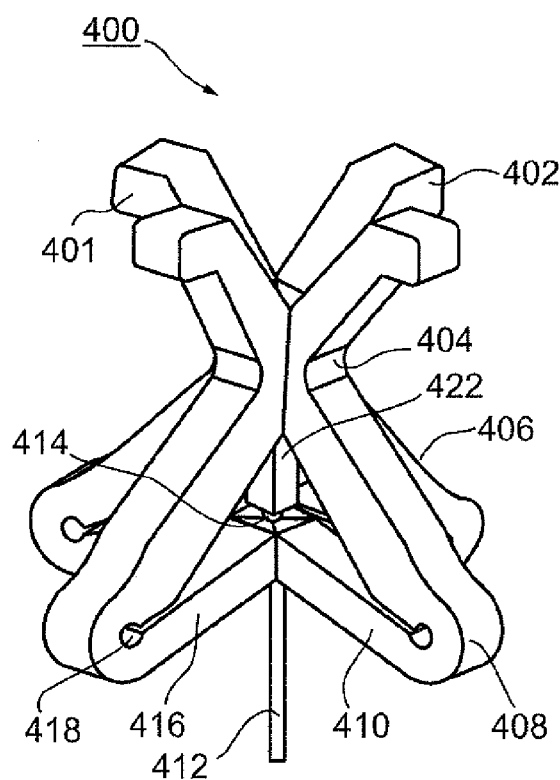
FIG. 4b is a perspective view of the bottom portion of the device of FIG. 4a illustrating the expansion element and its connection to support arms in a position in which it would normally contact the vaginal wall and be slightly constricted thereby.
Figure 4D:
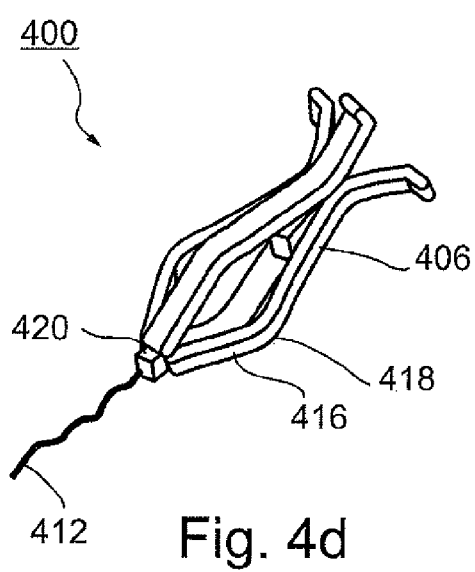
FIG. 4d is a perspective view of the device of FIG. 4a in a collapsed state achieved by application of an external force.
Figure 4C:
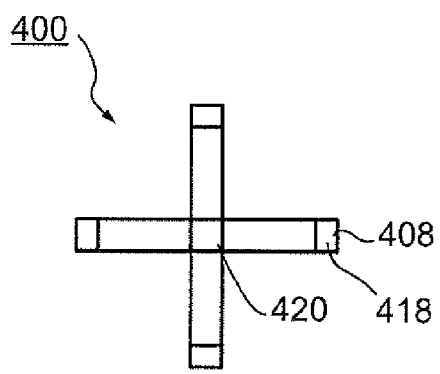

FIGS. 4a, 4b and 4c depict an exemplary device 400 in which support arms 406 and support elements 416 of expansion mechanism 410 are formed as a continuous piece. The anchoring portion of exemplary device 400 is similar to that described hereinabove for other embodiments. Briefly, the anchoring portion comprises a plurality of legs 401 which terminate in feet 402 at their distal ends. Legs 401 converge at neck 404 which is also joined to support arms 406.

FIG. 4a is a side view of exemplary device 400 in its normally open position. FIG. 4b is a perspective view of the bottom portion of device 400 illustrating expansion element 410 and its connection to support arms 406 more clearly. FIG. 4c is a bottom view of device 400 in its normally open position.

FIG. 4d is a perspective view of device 400 in its closed position. Depicted exemplary device 400 comprises an expansion mechanism 410 comprising four arcs 416 integrally formed with support arms 406. A "hair pin" flexible spring hinge 418 is interposed between each arc 416 and corresponding support arm 406. In an exemplary embodiment of the invention, material used to construct arms 406 and support elements 416 is characterized by a springlike memory so that device 400 naturally tends towards the open operational state depicted in FIG. 4a. Optionally, the configuration of hinges 418 contributes to this tendency. In the depicted embodiment, post 422 limits motion of expansion mechanism 410 inwards towards anchor leg 401. Limitation of motion can be important, for example during sudden vaginal contraction (e.g. during a cough or sneeze). In an exemplary embodiment of the invention, a height of post 422 is selected to insure a minimum radius defined by hands 408 in response to a convergent force applied thereto.

In the depicted embodiment curves between support arm 406 and arc 416 form "hands" 408 which engage the vaginal wall during use.

In the depicted embodiment, a string 412 is connected to a flexible hub 420 at the intersection of the four support elements 416, optionally by anchor 414. Anchor 414 can be employed in embodiments with string 412 of fixed diameter fitted to a fixed diameter channel in hub 420. As described above for other exemplary embodiments, a pull of string 412 causes device 400 to change from the normally open configuration of FIGS. 4a, 4b and 4c to the closed configuration of FIG. 4d. In the closed position, hinges 418 are opened so that arcs 416 become extensions of arms 406. Optionally, hinges 418, and/or 420 contribute to a flexibility of device 400 which allows transition from the normally open to the closed operational state as described above for other exemplary embodiments.

In an exemplary embodiment of the invention, device 400 in the normally closed position exerts a predefined force against vaginal walls via hands 408 which optionally define a curve of desired dimensions.

In an exemplary embodiment of the invention, flexibility of hinges 418 contributes to ease of removal.

In an exemplary embodiment of the invention, legs 401, neck 404, arms 406 and support elements 416 are cast or molded as a single piece.

In an exemplary embodiment of the invention, hinge 418 adjacent to hand 408 is subject to tension and support elements 416 are relaxed when device 400 is stored in the collapsed configuration of FIG. 4d (e.g. within an applicator). When device 400 is deployed, the situation is reversed so that hinge 418 is relaxed and support elements 416 are subject to constrictive forces applied by the vagina. In an exemplary embodiment of the invention, this change in force distribution contributes to a long storage life without any significant adverse effect on device performance after deployment.

Exemplary Normally Open Expansion Elements Formed by Assembly

Exemplary embodiments of the invention described below are formed by assembly of component pieces. The assembled pieces form a normally open device functionally similar to embodiments described above. Optionally, assembly of pieces contributes to a reduction in manufacturing costs. Optionally, reduction in manufacturing cost is related to the fact that each piece is made from a single material. In an exemplary embodiment of the invention, an elastic loading element incorporated into the assembled device urges the device towards a normally open position.

FIG. 5a is a perspective view of an exemplary device 500 in its normally open position. Exemplary device 500 is assembled from component pieces as described hereinbelow. In an exemplary embodiment of the invention, support arms 566 are nearly always straight. In an exemplary embodiment of the invention, hub 519 and/or expansion struts 516 contribute to resiliency of support arms 566.

During intra-vaginal use, device 500 is typically in this position. Device 500 comprises an anchor section including an anchor body 513 and a plurality of anchor legs 521. In the depicted embodiment, each leg 521 terminates in a foot 511. Depicted exemplary device 500 also comprises a support section comprising support body 530 and a plurality of support arms 566. In the depicted embodiment, each arm 566 terminates in a support hand 580.

In an exemplary embodiment of the invention, the support section of device 500 is manufactured separately from the anchor section of the device. In FIGS. 5a, 5b and 5c, seam 540 indicates joining of the two sections, optionally in a post manufacturing process.

In an exemplary embodiment of the invention, device 500 comprises an expansion mechanism 510 comprising a plurality of expansion struts 516 joined at a hinged hub 519. In the depicted embodiment, each strut 516 terminates in a hinge pin 518 adapted to mate to a hinge slot 590 in hand 580 of corresponding arm 566.

Optionally, expansion struts 516 are configured as elastic bars (e.g. silicone or polyurethane,). In an exemplary embodiment of the invention, hinged hub 519 is configured as a dome-shaped body. Optionally, hub 519 comprises grooves 523. In an exemplary embodiment of the invention, each groove 523 engages an edge of a corresponding support arm 566 when device 500 is in the normally open configuration of FIG. 5a. Optionally, this engagement provides additional support and/or strength and/or reduces a tendency towards movements of arms 566, for example by shortening arms 566 so that they become stiffer.

In the depicted embodiment, each strut 516 includes two integral hinges. A first hinge 520 connects each strut 516 to hub 519. A second hinge 518 facilitates attachment to hand 580 of support arm 566 (e.g. via insertion in hinge slot 590 as depicted).

In an exemplary embodiment of the invention, expansion mechanism 510 is not manufactured as an integral portion of device 500. Optionally, expansion mechanism 510 is attached to hands 566 (e.g. to hands 580) during a process of assembly.

FIG. 5c is a side view of device 500 in a closed operational state. The depicted closed operational state is suitable for vaginal insertion, with feet 511 of legs 521 being inserted first. In an exemplary embodiment of the invention, an applicator (e.g. a cardboard cylinder; not shown) holds device 500 in the closed operational state. Optionally, the applicator also radially collapses anchor legs 521 to the depicted closed operational state. In the closed operational state, hub 519 is at its maximum distance from seam 540.

Upon insertion of device 500 in the vagina and removal of the applicator, device 500 assumes the open-unlocked operational state of FIG. 5b.

In order to achieve the open locked operational state of FIG. 5a, the user pulls on string 512 which is connected to the anchor portion of the device. In an exemplary embodiment of the invention, string 512 is either elastic or has an elastic section. Pulling string 512 causes engagement protrusion 514 (e.g. a knot in, or a ring upon, string 512) to move towards, and eventually engage, retention channel 522 of hub 519. Optionally, the user perceives engagement of protrusion 514 by retention channel 522 either audibly (e.g. a click or pop) or by means of increased resistance to pulling. In an exemplary embodiment of the invention, the perceived engagement conforms that device 500 is loaded and/or ready for use.

After engagement of protrusion 514 by retention channel 522, the user releases string 512 and the elasticity of string 512 pulls hub 519 towards support section base 550. In an exemplary embodiment of the invention, hinges 518 and 520 move to accommodate this motion of hub 519. In an exemplary embodiment of the invention, when hub 519 contacts base 550, grooves 523 engage arms 566. At this stage, device 500 is in its normally open position.

In order to adjust a position of, and/or remove, device 500, string 512 can be pulled again to move hub 519 away from base 550, optionally until the support section of device 500 comes to the fully closed position of FIG. 5c.

Optionally, the transition from the configuration of FIG. 5c to that of FIG. 5a causes hands 580 transiently expand radially outwards to a degree that is perceptible to the user. In an exemplary embodiment of the invention, user perception of the radial expansion and its cessation serves as a signal that a sufficient tension has been applied to handle (e.g. string 512) to facilitate repositioning. Optionally, this transient radial expansion is perceived again after string 512 is released and serves as an indication that device 500 has been "seated" in its new position. Optionally, radial expansion of 4, 6, 8 or 10 mm or intermediate or greater distances is perceptible to the user without causing clinically significant tissue damage. In some embodiments of the invention, in devices according to various of the Figures shown herein, the expansion is un-noticed and/or does not exist.

In an exemplary embodiment of the invention, tendency to move "cross center" from the open unlocked position (FIG. 5b) to the stable open locked position (FIG. 5a) depends on an amount of energy stored within an elastic portion of string 512 as protrusion 514 is made to engage retention channel 522. In an exemplary embodiment of the invention, a significant portion of this stored energy is dissipated as hub 519 travels towards support section base 550.

Figure 5D:
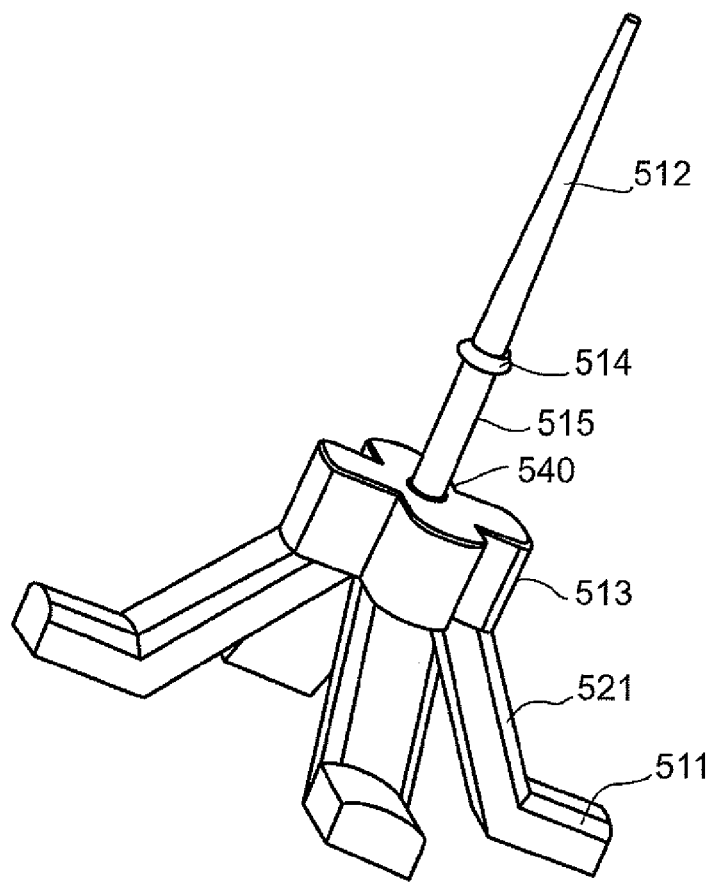
FIG. 5d is a perspective view of an anchor portion of the device of FIG. 5a removed from the device.

FIG. 5d is a perspective view of an anchor portion of device 500 removed from the support section. In FIG. 5d an exemplary elastic section 515 of string 512 is visible between protrusion 514 and anchor base 513. In the depicted embodiment, elastic section 515 of string 512 is attached to anchor base 513 via a string lumen 540 which passes at least partly through base 513. Optionally, a transverse anchor (not pictured) passes through lumen 540 and elastic portion 515 of handle 512 (e.g. a string) to provide a strong connection to base 513. Optionally, an inelastic portion of string 512 can be replaced by a pole, rod or other graspable element.

Figure 5E:
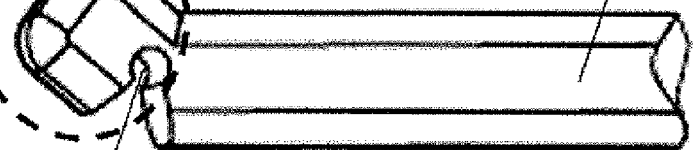
FIG. 5e is a side view of a support arm of FIG. 5a removed from the device depicting clearly a groove for connecting to the expansion element.

FIG. 5e is a side view of a portion of exemplary support arm 516 removed from device 500 clearly depicting groove 590 in hand 580 of support arm 566 adapted to engage hinge pin 518 of expansion strut 516. Optionally, thinning 595 provides added flexibility and/or reduces weight while conserving strength.

Optionally, device 500 can be stored in the unloaded state of FIG. 5e. In an exemplary embodiment of the invention, hinges of exemplary device 500 are not subject to stress during storage because the device is pre-loaded slightly prior to use.

Figure 6A:
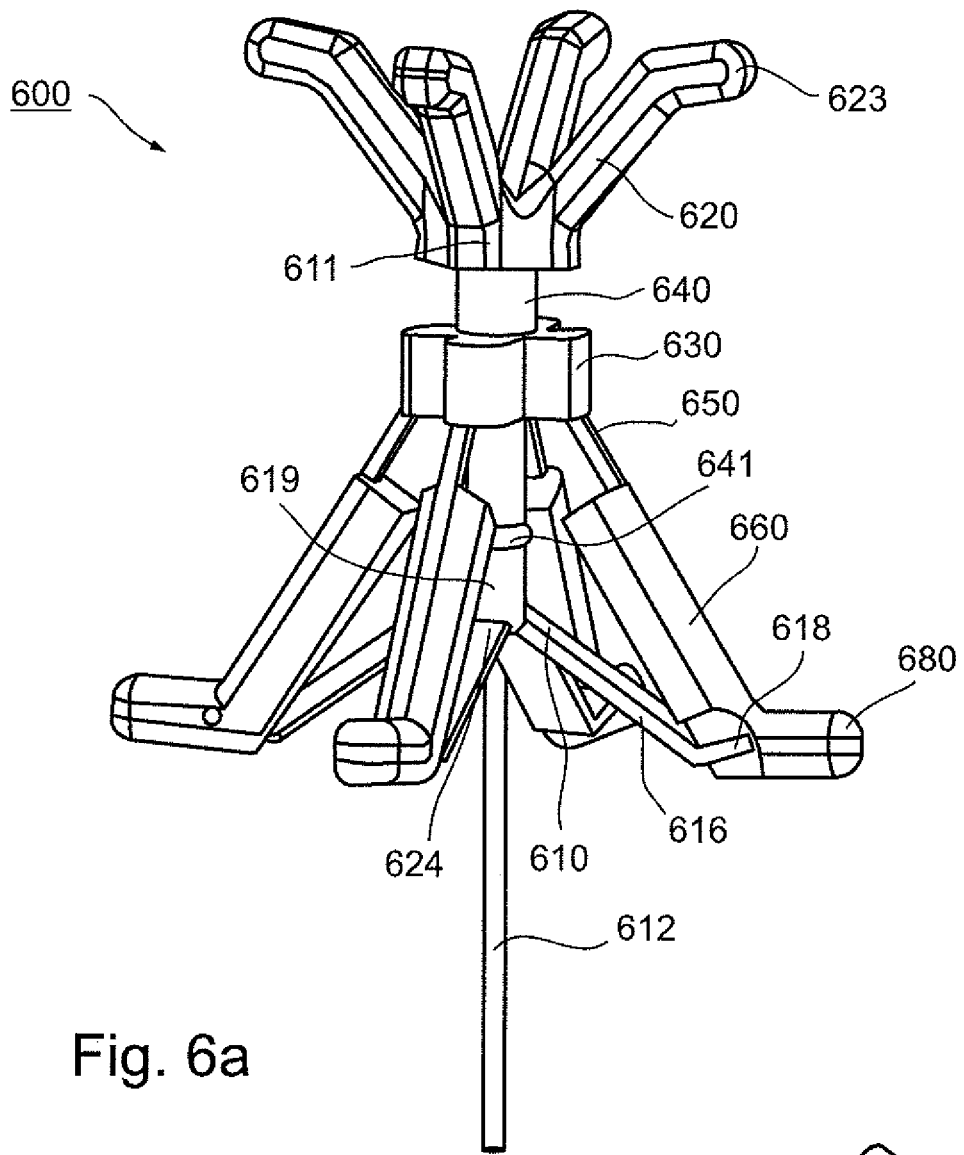
FIG. 6a is a side view of an exemplary device according to another exemplary embodiment of the invention in its normally open position.

FIG. 6a is a side view of an additional exemplary device 600 according to another exemplary embodiment of the invention in its normally open position. In the depicted embodiment expansion mechanism 610 comprises a separate apparatus including four plastic (rigid) bars (e.g. polypropylene) 616 which converge at a tubular hub 619. In the depicted embodiment, tubular hub 619 is connected to each of bars 616 by an integral hinge 624. In the depicted embodiment, each bar 616 is connected at its opposite end to a support arm 660 by means of a non integral hinge 618. Optionally, support arms 660 are constructed of a flexible material, such as silicon. For purposes of this specification and accompanying claims, an "integral hinge" comprises a hinge constructed of a same, contiguous material as adjacent portions of the device which are subject to angular displacement with respect to the hinge. Integral hinges are sometimes referred to a living hinges.

Figure 6B:
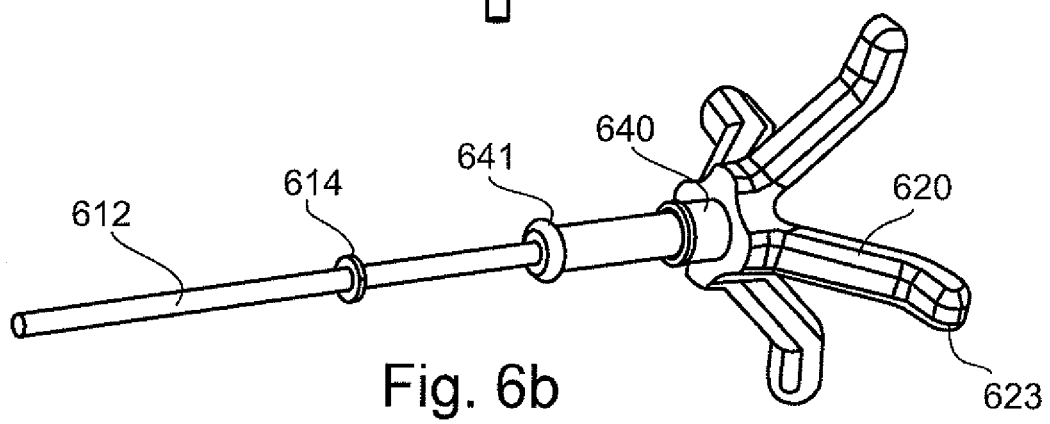
FIG. 6b depicts the anchor portion of the device of FIG. 6a removed from the device.
Figure 6C:
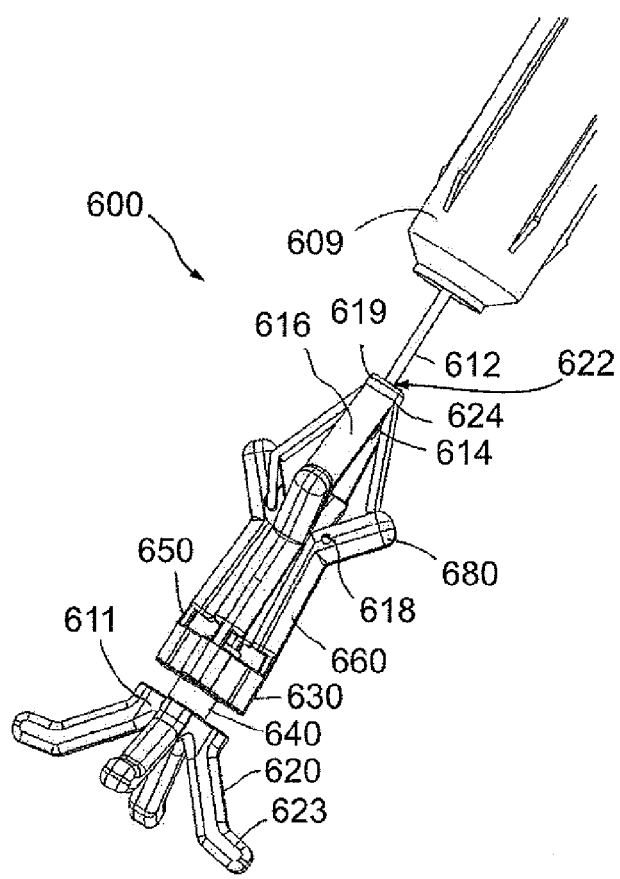
FIG. 6c is a perspective view of the device of FIG. 6a in a collapsed state achieved by application of an external force.
Figure 6D:
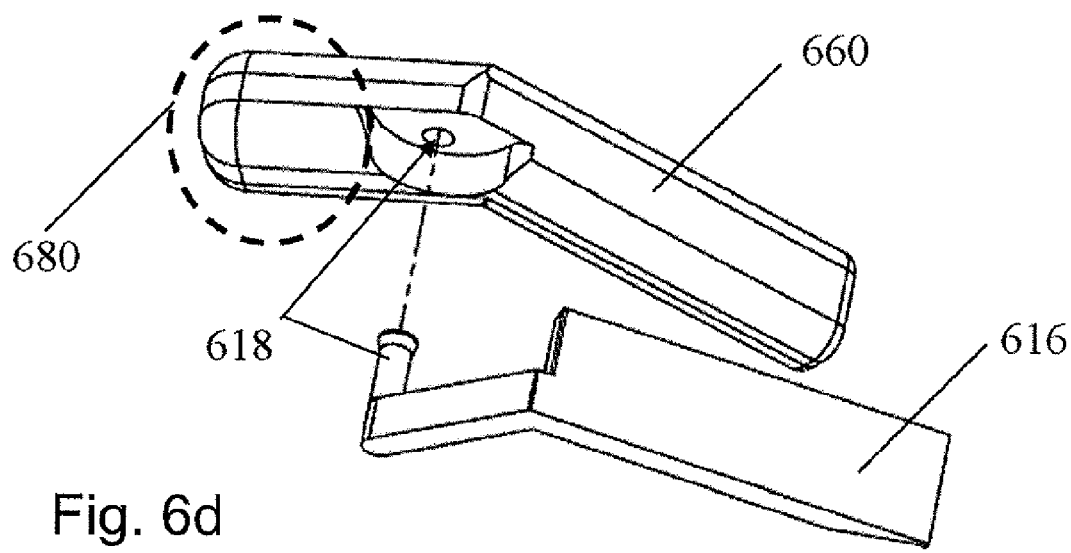
FIG. 6d is an exploded view of a support arm and a corresponding portion of an expansion element, depicting a hinged attachment therebetween in greater detail.

FIG. 6d is an exploded view of support arm 660 and a corresponding portion of bar 616, depicting hinged attachment 618 therebetween in greater detail.

Device 600 comprises an anchor section including an anchor base 611 and a plurality of anchor legs 620 each optionally terminating in a foot 623. In the depicted embodiment, an anchor neck 640 protrudes through an engagement ring 630 and terminates in a flange 641. Optionally, engagement ring 630 is axially stationary and/or rotatable with respect to anchor neck 640. Optionally, anchor neck 640 is flexible.

FIG. 6b depicts the anchor portion of device 600 removed from the device. In this view an activation handle (e.g. a string) is seen to protrude from the flanged end (641) of anchor neck 640.

Referring again to FIG. 6a, device 600 comprises a support section. The support section comprises a ringed support base 630 through which anchor neck 640 passes. In an exemplary embodiment of the invention, a plurality of support arms 660 are attached to ring 630 by hinges 650. Optionally, each arm terminates in a hand 680 adapted to apply a predefined force to a vaginal wall.

In the depicted embodiment, expansion mechanism 610 engages flange 641 of anchor neck 640 by tubular hub 619. Activation handle 612 is attached to (e.g. by passing through) tubular hub 619 and is available for manual activation.

FIG. 6c is a perspective view of the device of FIG. 6a in a collapsed state achieved by application of an external force (e.g. an applicator 609). In this collapsed state, expansion elements 616 are extended beyond hands 680 of support arms 660.

Prior to deployment from applicator 609, the user pulls handle 612 (e.g. a string), which is at least partially elastic. Pulling handle 612 brings protrusion 614 to engagement groove 622 of tubular hub 619 where protrusion 614 is engaged and retained. Release of string 612 after deployment of device 600 from applicator 609 allows an elastic portion of handle 612 to pull tubular hub 619 towards flange 641 of anchor neck 640 where it seats, optionally locking thereto. Seating of tubular hub 619 on flange 641 produces a force sufficient to overcome elastic contraction of handle 612. In an exemplary embodiment of the invention, handle 612 is elastic only\ in the section between 614 and 641 (see FIG. 6b).

At this stage, device 600 is in the normally open position of FIG. 6a. In an exemplary embodiment of the invention, pulling on string 612 causes tubular hub 619 to move away from flange 641 and can allow repositioning and/or removal of device 600. In an exemplary embodiment of the invention, applicator 609 is a self lubricating applicator, for example of the type described in WO 2006/097935, the disclosure of which is fully incorporated herein by reference. Alternatively, other known applicator types can be adapted for use in the context of embodiments of the invention by one of ordinary skill in the art.

Exemplary device 600 share many of the properties of exemplary device 500 as described above.

Exemplary Modular Expansion Element

FIGS. 7A, 7b, 7c and 7d depict an exemplary embodiment of the invention in which an expansion mechanism 710 and anchor base 711 are provided as separate pieces to be assembled with pieces of standard tubing 760 (e.g. silicone or other flexible plastic) to form another additional exemplary device 700. In an exemplary embodiment of the invention, tubing 760 is separate from mechanism 710. Optionally, tubing 760 defines both an anchor and a support. Optionally, use of flexible tubing 760 reduces manufacturing costs of device 700 and/or contributes to an ability to use different combination of expansion mechanism 710 and/or anchor base 711 and or tubing to create devices 700 with different dimensions and/or properties.

In an exemplary embodiment of the invention, use of tubing of different lengths and/or diameters with a single expansion mechanism 710 and/or anchor bases 711 of different sizes/configurations produce a series of different devices 700 characterized by different sizes and/or configurations and/or degrees of flexibility. Optionally, device 700 is tailored to a specific patient or patient size at time of manufacture or assembly. In an exemplary embodiment of the invention, tailoring can be by selection of diameter and/or length and/or wall thickness of tubing 760.

FIG. 7a is a side view of device 700 in its closed operational state (e.g. when loaded in an applicator). Device 700 is similar to exemplary embodiments described hereinabove in that is normally open.

The anchor section of exemplary device 700 comprises four flexible plastic tubes 760 held together by anchor base 711 and support base 730. In an exemplary embodiment of the invention, anchor base 711 and support base 730 are integrated into a single piece. Portions of tubing 760 between anchor base 711 and support base 730 comprise anchor neck 740. Portions of tubing 760 extending beyond anchor base 711 comprise anchor legs 724. Optionally, outward deflection of legs 724 to form anchor feet as pictured results from pretreatment of tubing 760 and/or from interaction between tubing 760 and anchor base 711.

The support section of exemplary device 700 comprises four support arms (tubing 760) terminating in hands 762. Depicted exemplary expansion mechanism 710 comprises four plastic bars 716 (e.g. a rigid plastic such as polypropylene or polyethylene) which converge at a central hub 719 where they are attached to hub plate 722. The structures depicted in FIG. 7 are exemplary only and do not limit the invention.

Figure 7C:
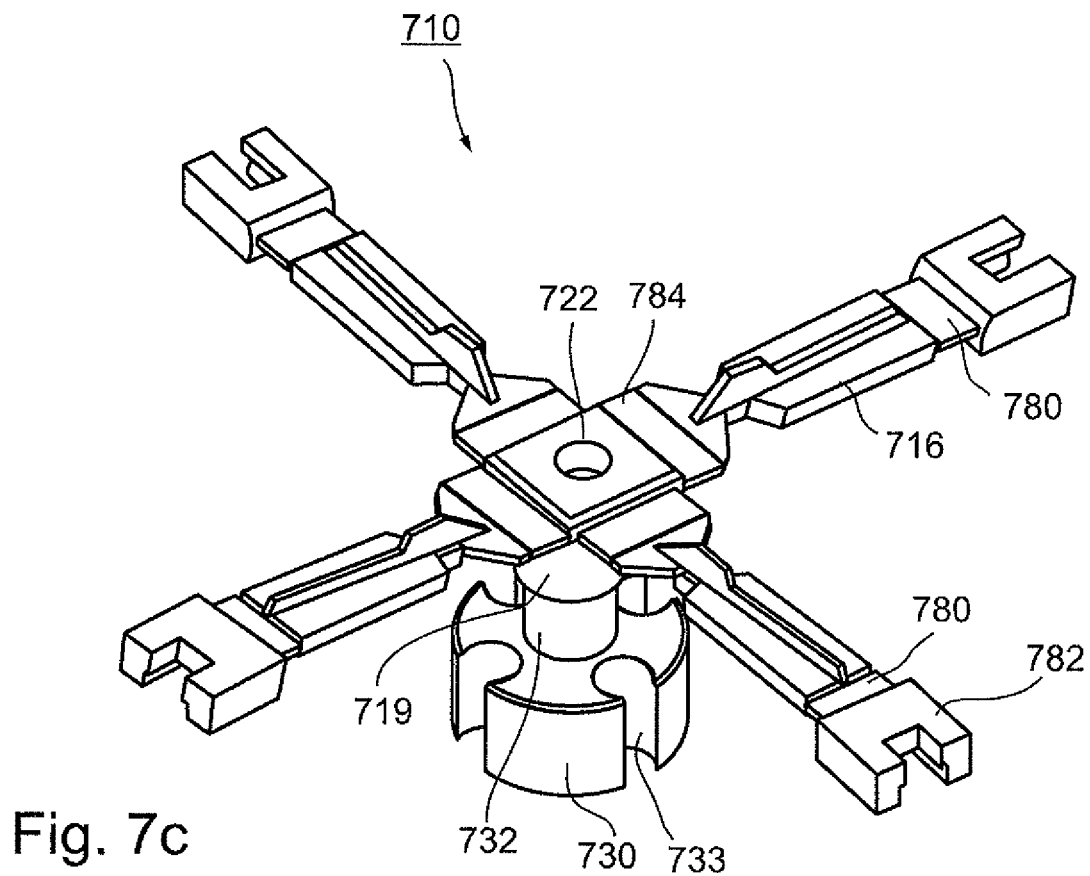
FIG. 7c is a perspective view of the expansion element of a device as depicted in FIG. 7a removed from the device.

FIG. 7c depicts expansion mechanism 710 removed from device 710 so that its component parts are not obscured by tubing 760. When spoke-bars 716 are straightened, tubular hub 719 is brought into contact with, and optionally engages, neck 732 of support base 730. Optionally, each bar 716 is aligned with a groove 733 in support base 730 as pictured. Grooves 733 are adapted to engage tubing 760 (not pictured in this view).

In an exemplary embodiment of the invention, each bar 716 comprises two or more hinges, optionally integral hinges. In the depicted embodiment, a first bar hinge 784 is proximal to plate 722 of hub 719 and a second bar hinge 780 is located near a distal end of bar 716. In an exemplary embodiment of the invention, a distal end 782 of each bar 716 is adapted to engage tubing 760. Adaptation for engagement can include, for example, a bifurcation as pictured. Optionally, one or more additional hinges are provided along the length of bar 716. First and second bar hinges 784 and 780 flex in opposite directions so that a main portion of bars 716 can remain straight while flexing tubing 760. In an exemplary embodiment of the invention, straight main portions of bars 716 provide structural rigidity along a portion of tubing 760 which functions as a support arm.

Figure 7D:
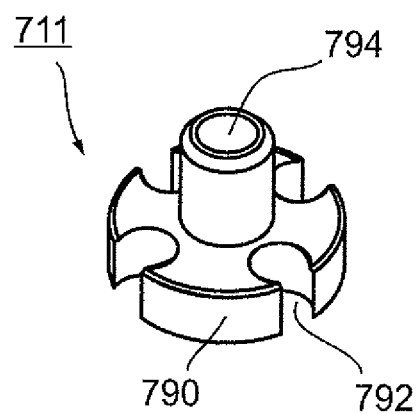
FIG. 7d is a perspective view of the anchor base of a device as depicted in FIG. 7a removed from the device.

FIG. 7D shows anchor base 711 separate from device 700. Depicted exemplary anchor base 711 comprises a disc-like body 790 with grooves 792 adapted to engage tubing 760 (not pictured in this view). Optionally, a connector 794 is attached to body 790. In an exemplary embodiment of the invention, connector 794 engages neck 732 and/or support base 730 of expansion mechanism 710. Optionally, engagement of connector 794 contributes to axial rigidity of the anchor section of device 700.

In an exemplary embodiment of the invention, anchor base 711 deflects anchor legs 740 radially outwards and/or holds several pieces of tubing in a desired orientation one to another. Optionally, base 711 engages other plastic parts.

Referring again to FIG. 7a, folding of bar hinges 780 and 784 while distal ends 782 of bars 716 engage hands 762 of support arm tubing 760 brings device 700 into its closed operational state. In the depicted closed operational state, expansion mechanism 710 is "outside" or "beyond" hands 762. Hub 719 is disengaged from neck 732 of support base 730 in this position. Optionally, hub 719 is attached to neck 732 by string 712.

In an exemplary embodiment of the invention, a handle 712 (e.g. a string), anchored in support base 730 extends through neck 732 and plate 722 of hub 719. Handle 712 comprises at least an elastic portion. In an exemplary embodiment of the invention, a protrusion 714 (e.g. a knot) is provided on handle 712. Optionally, the elastic portion of handle 712 is located between protrusion 714 and neck 732.

In an exemplary embodiment of the invention, a short time prior to use, the user prepares device 700 for opening by pulling string 712 with sufficient force to lengthen the elastic portion thereof. This pulling causes protrusion 714 to move towards plate 722 of hub 719. In an exemplary embodiment of the invention, plate 722 engages and retains protrusion 714. When the user releases string 712, the elastic portion of the string pulls hub 719 towards neck 732 of support base 730 and expansion mechanism 710 is activated.

FIG. 7b depicts device 700 in its normally open operational state. Hub 719 has approached neck 732 of support base 730 and support arm tubing 760 has been flexed outward so that hands 762 contact vaginal walls with a desired degree of force. Optionally, hub 719 is held in proximity to neck 732 by string 712 or locks to neck 732.

In an exemplary embodiment of the invention, use of tubes 760 in conjunction with separately manufactured expansion mechanism 710 and support base 711 contribute to a reduction in cost of device 700. Optionally, tubing 760 is extruded in a continuous process and cut to desired lengths.

In an exemplary embodiment of the invention, feet 724 of anchor legs 740 are curved and/or thickened. Optionally, curving and/or thickening can be achieved by thermal and/or chemical treatment and/or by use of pre-shaped inserts within the tubing.

In an exemplary embodiment of the invention, grooves 733 and/or 792 and/or bifurcations 782 engage tubing 760 with sufficient force that tubing 760 neither falls out nor slips axially with respect to these parts. Optionally, sufficient force is provided by a width of these parts relative to tubing diameter. Optionally, insertion of tubing 760 into grooves 733 and/or 792 and/or bifurcations 782 produces an audible and/or tactile click.

In an exemplary embodiment of the invention, device 700 is inserted in an applicator (not pictured) while in the closed operational state of FIG. 7a.

Exemplary Control of Collapse of an Optional Cover

FIGS. 1f, 1g, 1h, 1i and 1j depict exemplary mechanisms for control of collapse of an optional cover for the device.

Figure 1F:
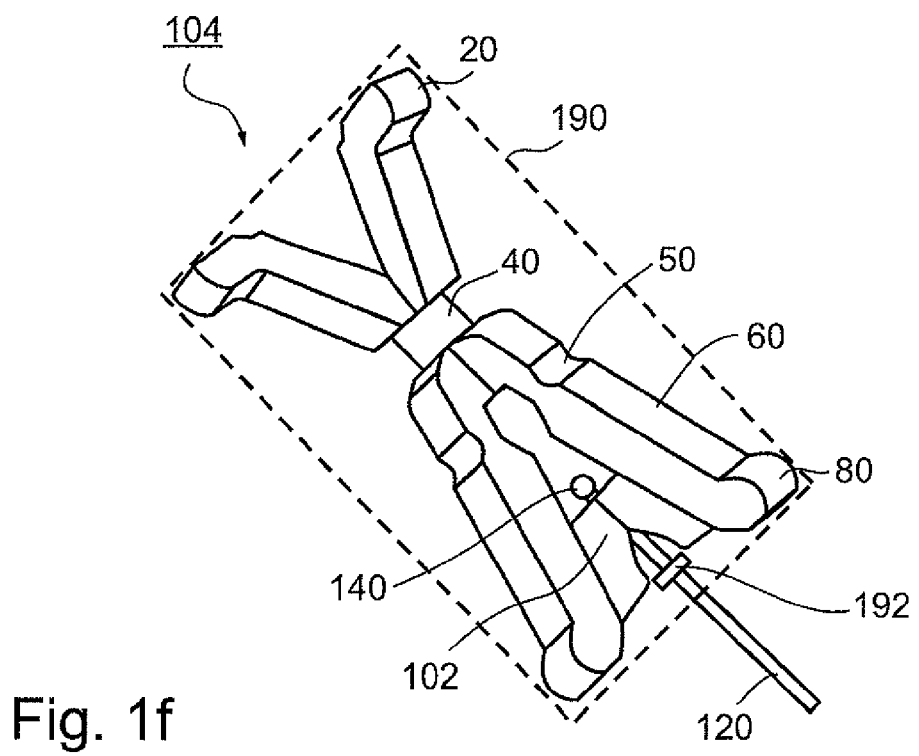
FIG. 1f is a perspective view of an exemplary device similar to FIG. 1a in its normally open state and equipped with a mechanism for control of collapse of an optional cover after collapse of the device itself.
Figure 1G:
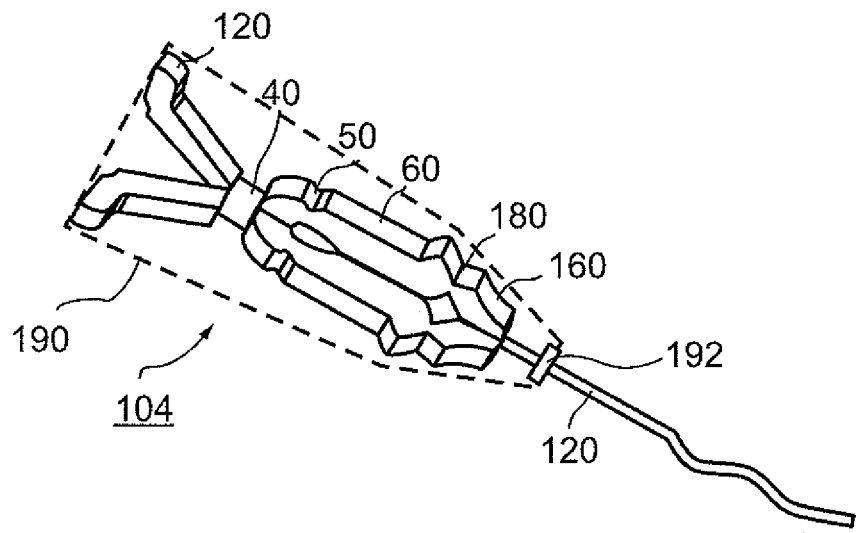
FIG. 1g is a side view of the exemplary of FIG. 1f in its collapsed state depicting shape change of the optional cover.

FIGS. 1f and 1g depict an exemplary device 104 encased by a cover 190. Device 104 is equipped with a single mechanism controlling collapse of cover 190 and support arms 60 of device 104. In the depicted embodiment, the single mechanism includes a handle (e.g. a string) 120 with a cover engaging element (e.g. a disc) 192 attached thereto. Depicted cover engaging element 192 is axially fixed with respect to depicted string 120. As depicted string 120 is pulled, expansion mechanism 102 exerts pressure on support arms 60. Support arms 60 respond by expanding radially outwards. Expansion mechanism 102 undergoes axial translation towards a plane defined by hands 80 of arms 60. During this axial translation, disc 192 comes into contact with cover 190 and exerts a deforming force thereupon.

FIG. 1g shows device 104 with cover 190 collapsed and arms 60 radially contracted. Arcs 160 of expansion mechanism 102 are axially extended and disc 192 holds cover 190 axially extended.

Figure 1H:
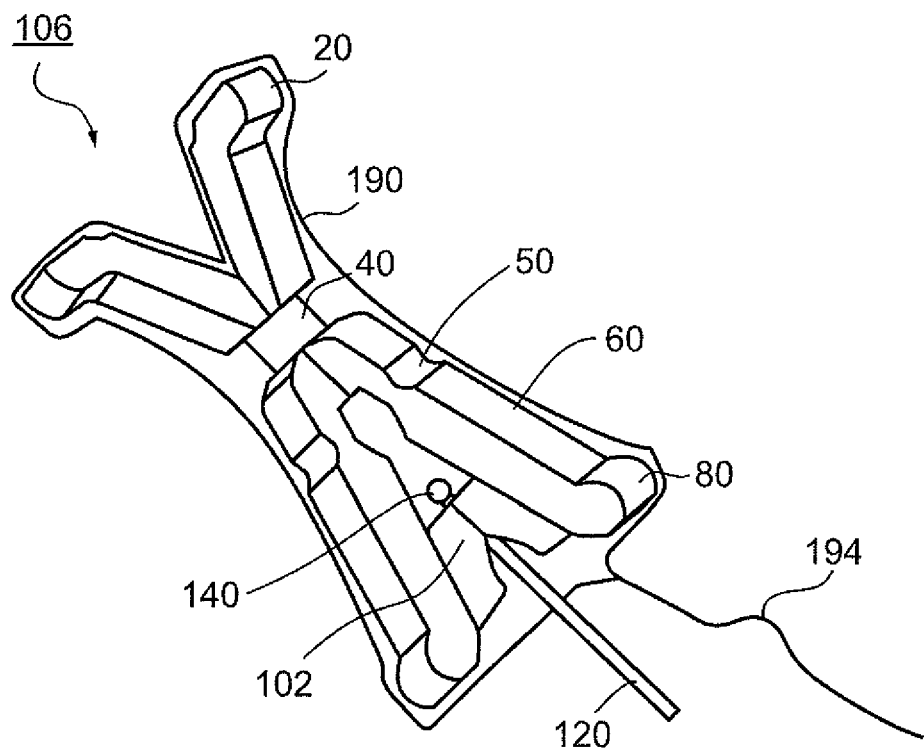
FIGS. 1h, 1i and 1j are side views of an exemplary device according to another embodiment of the invention in which an optional cover is collapsed via a separate control mechanism from the device itself in normally open, device collapsed/cover open and device collapsed/cover collapsed states respectively.
Figure 1I:
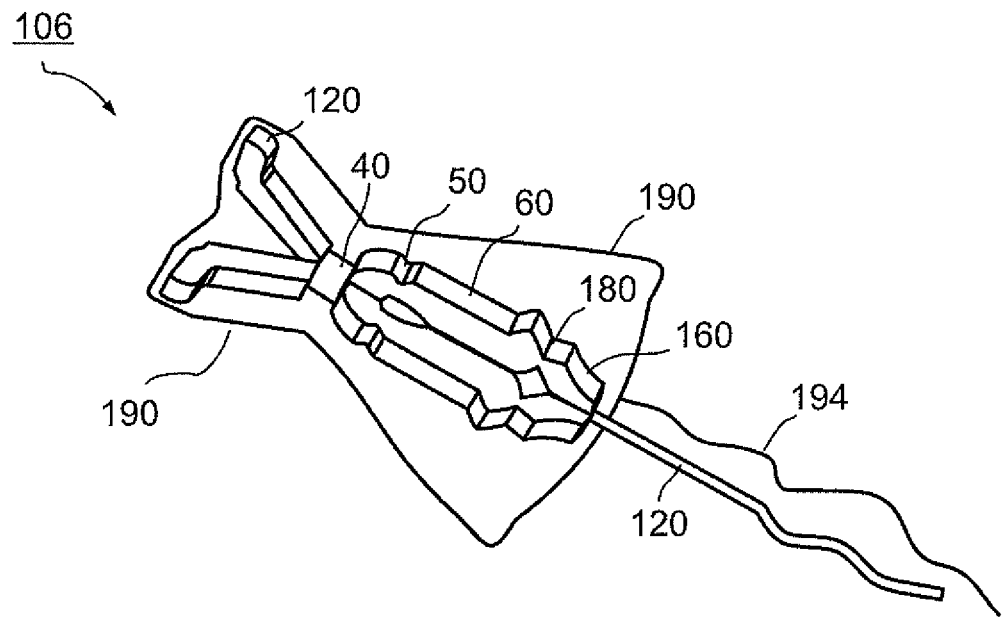
Figure 1J:
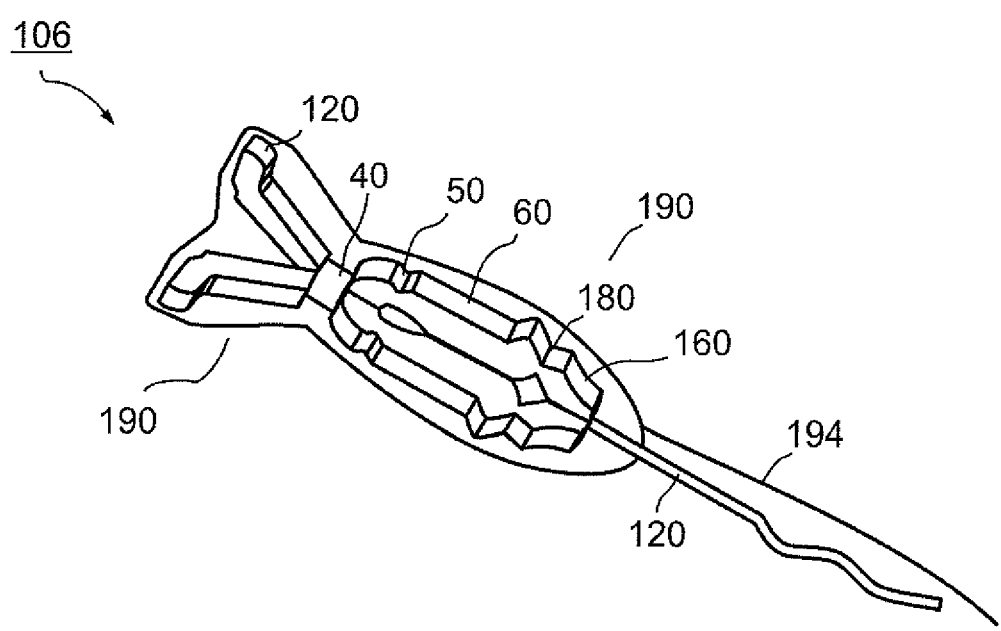

FIGS. 1h, 1i and 1j depict another exemplary device 106 encased by a cover 190. Device 106 is equipped with a first mechanism (string 120) controlling collapse of support arms 60 of device 104 substantially as described above. In the depicted embodiment, a second mechanism (depicted as string 194) governs collapse of cover 190 independent of the first mechanism. As in the embodiment described above, tension on string 120 exerts pressure on support arms 60 which respond by expanding radially outwards as expansion mechanism 102 undergoes axial translation towards a plane defined by hands 80 of arms 60.

FIG. 1i shows that eversion of expansion mechanism does not cause any change in the conformation of cover 190.

FIG. 1j shows that tension applied to string 194 causes cover 190 to collapse and conform to device 104 with cover 190 collapsed and arms 60 radially contracted. Arcs 160 of expansion mechanism 102 are axially extended.

Optionally, a dual mechanism configuration as depicted in device 106 offers greater control over coordination of collapse of cover 190 and the device than the single mechanism configuration of device 104. However, users may find the single mechanism of device 104 easier to operate.

Exemplary Scissor Type Expansion Mechanism

Figure 8:
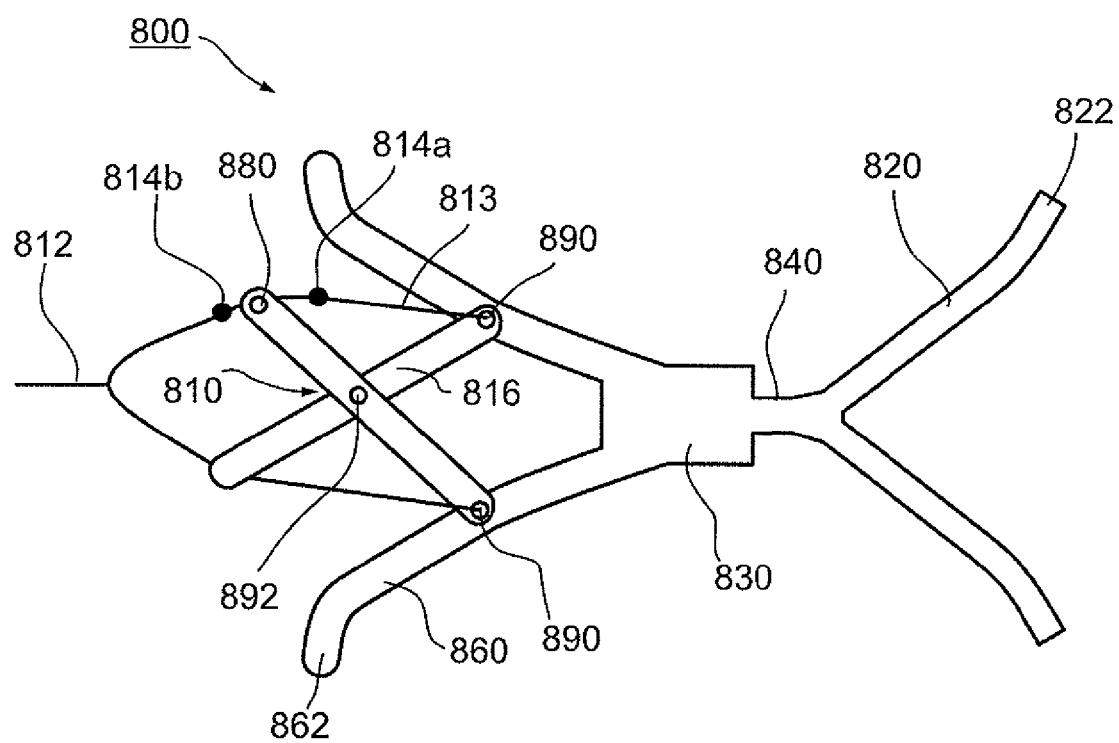
FIG. 8 is a side view of an exemplary device according another exemplary embodiment of the invention.

FIG. 8 is a side view of an exemplary device 800 featuring a scissors type expansion mechanism 810 according to another exemplary embodiment of the invention. In the depicted embodiment, mechanism 810 comprises two expansion levers 816 joined to one another by an expansion hinge 892. Additional hinges 890 secure the levers 816 to support arms 860 which optionally terminate in hands 862.

In an exemplary embodiment of the invention, tension in an elastic cord 813 urges hinge 892 towards a line connecting hinges 890 so that support arms 860 assume a normally open configuration. Optionally, protrusion 814b (e.g. a knot) limits a degree to which elastic cord 813 can retract through groove 880 or serves as a bump that makes it less likely to slip back past if string 812 is released.

In an exemplary embodiment of the invention, anchor legs 820, optionally comprising feet 822 are intra-vaginally inserted from an applicator and expand to anchor device 800. In an exemplary embodiment of the invention, support arms 860 are coupled to the anchor section by anchor base 840 and/or support base 830 which are optionally rotationally translatable with respect to one another.

In an exemplary embodiment of the invention, support arms 860 expand to their normally open position after ejection from the applicator is complete.

In an exemplary embodiment of the invention, a repositioning handle 812 (e.g. a string) is provided attached to string 813. Pulling on string 812 can collapse arms 816 with respect to hinge 892. Collapse of arms 816 urges arms 860 to close axially. Axial closing of arms 816 can be useful to reposition and/or remove device 800. Optionally, protrusion contributes to axial closing by limiting a degree to which elastic cord 813 can pass through groove 880 in expansion lever 816.

In an exemplary embodiment of the invention, a scissors-like expansion mechanism as exemplified by FIG. 8 contributes to a reduction in interference of the expansion mechanism with the vaginal wall and/or provides increased mechanical advantage by application of leverage. Optionally, the scissors apply radial force to support arms 860. In an exemplary embodiment of the invention, a position of hinges 890 on arms 860 is selected to produce a desired mechanical force on arms 860 when string 812 is pulled.

Exemplary Mono-block Device

Figure 9A:
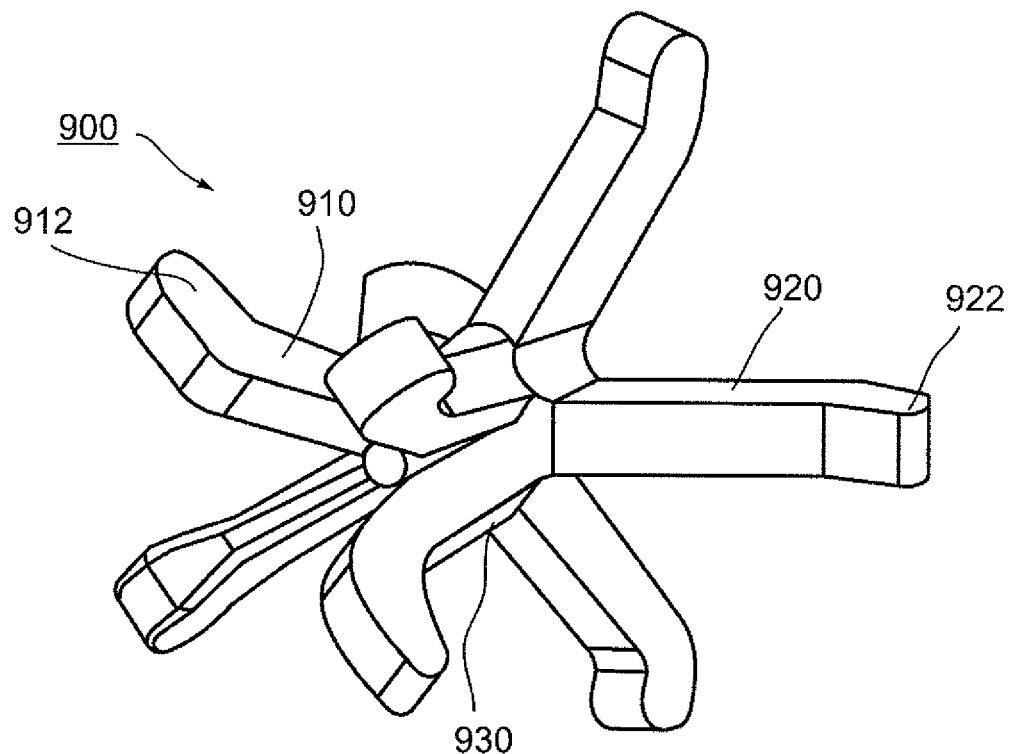
FIG. 9a is a perspective view of an exemplary device according to another exemplary embodiment of the invention in its normally open state.
Figure 9B:
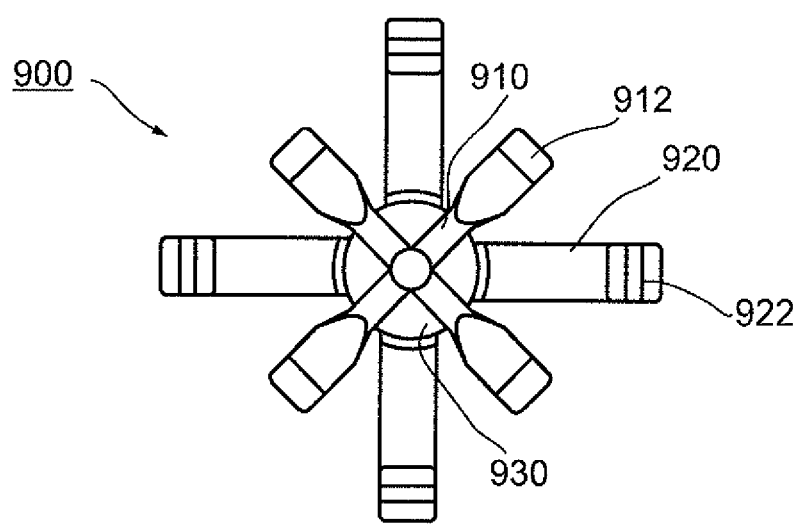
FIG. 9b is a top view (from anchor side) of the exemplary device of FIG. 9a illustrating rotational offset of anchor legs and support arms.

FIGS. 9a and 9b depict an exemplary device 900 according to another embodiment of the invention. FIG. 9a is a perspective view and FIG. 9b is a top view (from the anchor side).

Depicted device 900 comprises a center hub 930 which connects a plurality of anchor legs 910 to a plurality of support arms 920. Optionally, each leg 910 terminates in a foot 912 and/or each arm 920 terminates in a hand 922.

In the depicted exemplary embodiment, device 900 is characterized by a rotational offset of anchor legs 910 and support arms 920. Optionally, rotational offset contributes to reduced production cost. In an exemplary embodiment of the invention, device 900 is cast or injection molded as a single piece. Optionally, a mold for device 900 with rotationally offset legs 910 and arms 920 is inexpensive and/or simple to manufacture. Alternatively, or additionally, a mold for device 900 with rotationally offset legs 910 and arms 920 contributes to ease of removing a cast device 900 from the mold.

Exemplary Two Part Device

Figure 10:
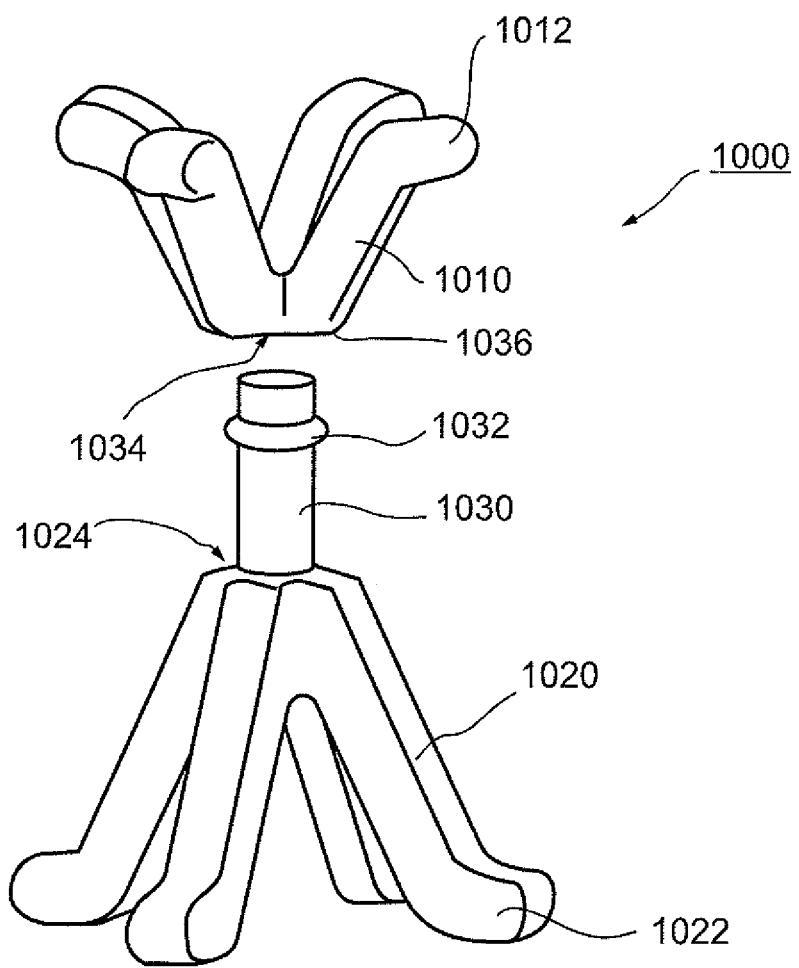
FIG. 10 is an exploded view of an exemplary device according to some embodiments of the invention featuring a "snap to fit" assembly mechanism.

FIG. 10 is an exploded view of an exemplary device 1000 manufactured in two pieces. Exemplary device 1000 comprises an anchor section with a plurality of anchor legs 1010. Optionally, each leg 1010 terminates in a foot 1012. Exemplary device 1000 also comprises a support section with a plurality of support arms 1020. Optionally, each arm 1020 terminates in a hand 1022.

In the depicted embodiment, the anchor section and support section are connectable by means of a "snap to fit" assembly mechanism. The snap to fit assembly mechanism comprises a neck 1030 protruding from a junction 1024 of arms 1020. Optionally, neck 1030 includes an engagement ridge 1032. Neck 1030 and/or ridge 1032 are adapted to enter, and be retained by, an engagement socket 1034 at junction 1036 of legs 1010.

In an exemplary embodiment of the invention, engagement of neck 1030 and/or ridge 1032 by socket 1034 fixes a rotational alignment between the anchor section and the support section. Optionally, engagement comprises one or more of physical contact, adhesive bonding, welding (e.g. ultrasonic) and asymmetric interference.

In an exemplary embodiment of the invention, rotation of the anchor section with respect to the support section is still possible after engagement of neck 1030 and/or ridge 1032 by socket 1034. Optionally, manufacture of a device in two pieces (e.g. device 1000) contributes to an ease of removing device parts from injection molds.

Optionally, manufacture of a device in two pieces (e.g. device 1000) contributes to an ability to customize a device for a particular patient by individually selecting anchor and support sections of different sizes.

Optionally, manufacture of a device in two pieces (e.g. device 1000) contributes to an ability to determine a rotational relationship between support arms and anchor legs after manufacture.

Exemplary Method of Use

Figure 11:
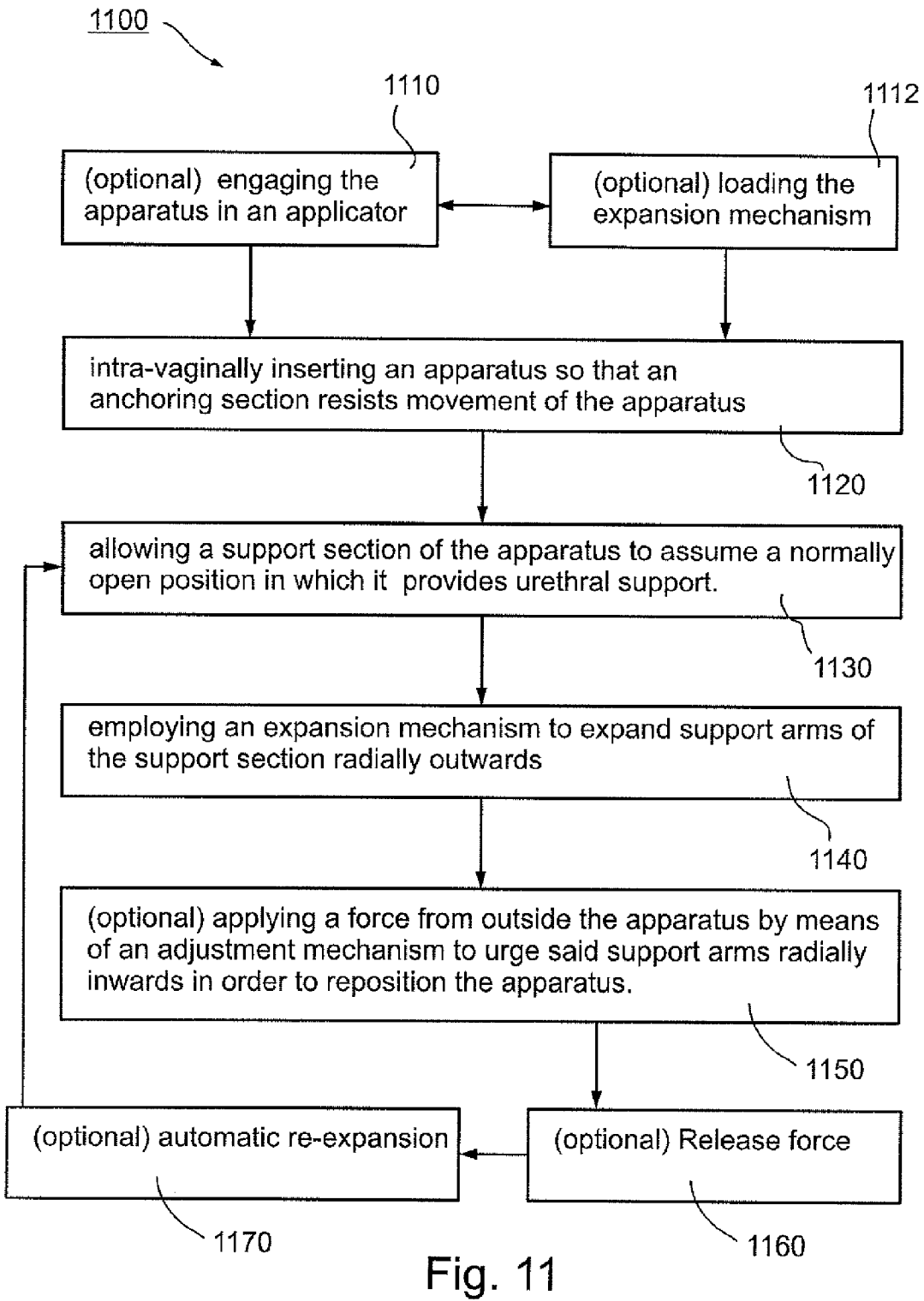
FIG. 11 is a simplified flow diagram of an exemplary method of ameliorating urinary incontinence in a female subject.

FIG. 11 is a simplified flow diagram of an exemplary method 1100 of ameliorating urinary incontinence in a female subject. Method 1100 optionally employs exemplary embodiments of apparatus as described hereinabove.

At 1100 the apparatus is optionally engaged in an applicator. In an exemplary embodiment of the invention, the applicator applies an external force to the apparatus. Optionally, the external force causes radial collapse of support arms from their normally open position.

At 1112, an expansion mechanism of the apparatus is optionally loaded (e.g. with an elastic string) as described above with regard to (for example) FIGS. 5b, 6c and 7b. Loading 1112 can optionally take place before or after engaging 1110 of the apparatus by the applicator. In an exemplary embodiment of the invention, loading 1112 is performed just prior to release of the apparatus from the applicator, At 1120 the apparatus is intra-vaginally inserted so that an anchoring section resists movement of the apparatus. If an applicator is employed, this process is concurrent with ejection of the apparatus from the applicator.

Once the apparatus is fully inserted in the vagina, a support section of the apparatus is allowed 1130 to assume a normally open position in which it provides urethral support. In an exemplary embodiment of the invention, urethral support is provided by a plurality of support arms which expand radially outwards.

In an exemplary embodiment of the invention, an expansion mechanism is employed 1140 to expand support arms of the support section radially outwards.

At 1150, a force from outside the apparatus can optionally be applied by means of an adjustment mechanism to urge said support arms radially inwards in order to reposition the apparatus. In an exemplary embodiment of the invention, the adjustment mechanism is congruent with the loading mechanism of 1112. Optionally, the external force is applied manually, for example by a user pulling on a string.

At 1160, the force is released causing automatic re-expansion 1170 of the support arms radially outward. This seats the device in its new position.

Exemplary Mechanical Model

Figure 12A:
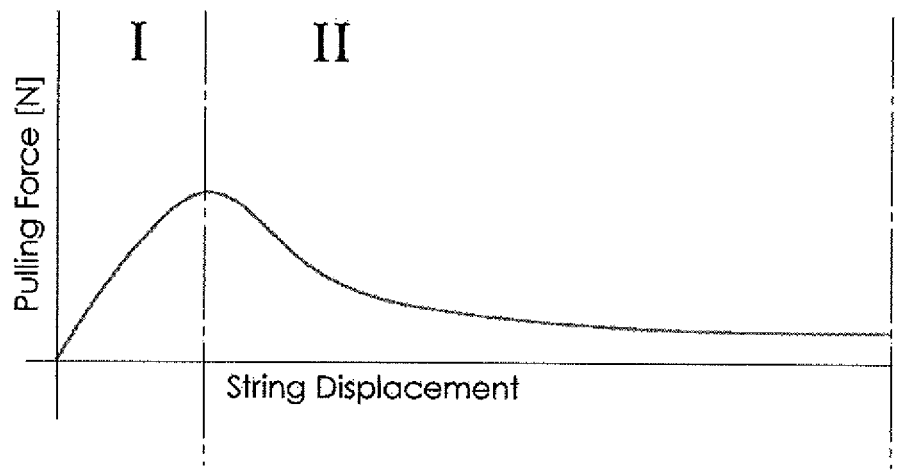
FIG. 12a is a graph of pulling force as a function of string displacement for an exemplary apparatus according to some embodiments of the invention.
Figure 12B:
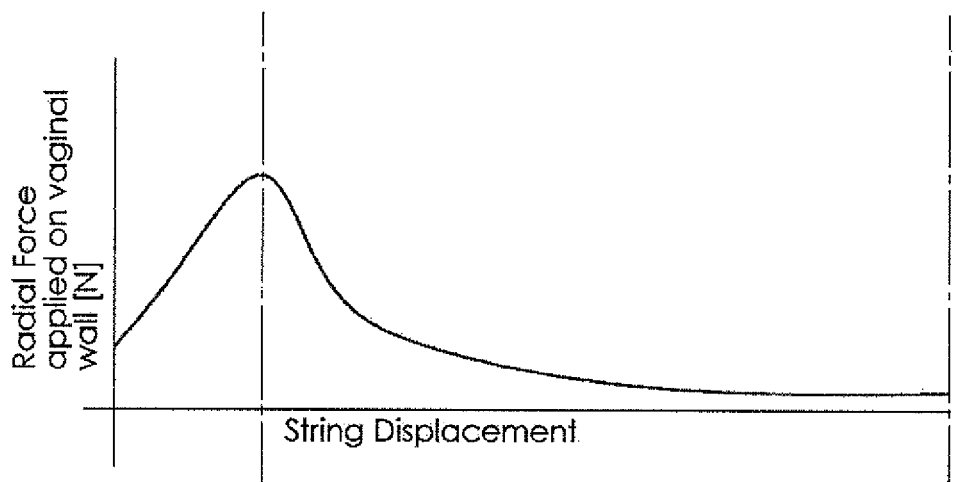
FIG. 12b is a graph of radial force applied on vaginal wall as a function of string displacement for an exemplary apparatus according to some embodiments of the invention.
Figure 12C:
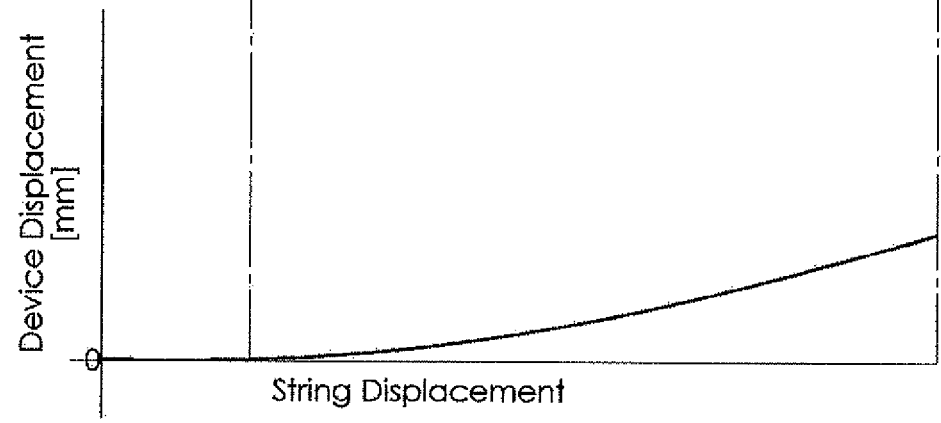
FIG. 12c is a graph of device displacement as a function of string displacement for an exemplary apparatus according to some embodiments of the invention.

FIGS. 12a, 12b and 12c are graphs illustrating mechanical response of an exemplary apparatus (e.g. 400) as a function of axially applied lengthening force according to some exemplary embodiments of the invention.

Using the exemplary embodiment of FIG. 4b as an example, and referring to the graph of FIG. 12b, arcs 416 of expansion mechanism 410 exert a high degree of radial expansion force. As string 412 is pulled to activate the conversion mechanism (hub) thereof and axially lengthen apparatus 400, the radial expansion force of arcs 416 increase (phase "I" in graph) until hub 420 passes through a plane containing hands 408 (FIG. 4a). At this point, there is a transition to phase "II" and the radial expansion force declines as device 400 moves towards the conformation depicted in FIG. 4d. In particular, the axial force applied to device is low and does not generally cause digging in of the arms of the device into the vaginal walls. In a device without a conversion mechanism (axial pulling pulls arms axially and thereby radially), the axial force increases as radial diameter is reduced, so there is a tradeoff between tendency to dig in due to radial diameter and tendency to dig in do to axial force. In the embodiment shown, the tendency to dig in is optionally reduced to better than half of that of a device without a hub.

FIG. 12a illustrates changes in the pulling force applied to string 412. The pulling force gradually increase, until the end of phase I, and then drops to a value needed to overcome the friction of the vagina against collapsed apparatus 400 and, in some embodiments, a relatively small contribution to overcome the elasticity of the conversion mechanism.

FIG. 12c illustrates axial extension, and/or collapse, of apparatus 400, from its normally open state, as string 412 is pulled. Although a pulling force is applied to string 412, apparatus 400 remains in place, and only internal movement of expansion mechanism 410 occurs until the end of stage I is reached. If application of pulling force to string 412 continues, apparatus 400 enters stage II and apparatus 400 slides towards the vaginal opening, optionally through the opening and out of the vagina.

When string 412 is released, normally open expansion mechanism 410 brings device 400 back through the position of FIG. 4a to the stable configuration of FIG. 4a.

In an exemplary embodiment of the invention, the force required in phase II (e.g., when at least 80%, 70%, 50%, 30% or intermediate amounts of available radial collapse and/or force reduction is provided) is less than 70%, 50%, 40%, 30%, 20% or intermediate values of the force required during phase I. In an exemplary embodiment of the invention, such ratios are provided when device anchor is held so that the axial force only causes radial collapse and/or radial reduction in force.

Optionally or alternatively, the force required in phase II is less than 70%, 50%, 40%, 30%, 20% or intermediate values of a reduction in radial outwards force applied by the support section in phase I.

Exemplary Ways of Fitting of a Device to a Patient

In some embodiments of the inventions, devices according to various designs described hereinabove are provided as "one size fits all" products.

Alternately, devices according to various designs described hereinabove are provided in several sizes (e.g. small, medium and large) in order to provide a good fit for all patients.

In other embodiment of the inventions, devices according to various designs described hereinabove are subject to different "custom fitting" plans.

One exemplary custom fitting plan employs exemplary devices of the type depicted in FIG. 10 in which the anchor section and support section are cast separately. Preparation of X sizes of anchor sections and Y sizes of support sections makes custom assembly of X*Y sizes of devices possible. For example if anchor sections are cast in 3 sizes (e.g. S, M and L), and support sections are cast in 3 sizes (e.g. S, M and L) a total of 9 device designs are possible:

| design | anchor | support |
| --- | --- | --- |
| 1 | S | S |
| 2 | S | M |
| 3 | S | L |
| 4 | M | S |
| 5 | M | M |
| 6 | M | L |
| 7 | L | S |
| 8 | L | M |
| 9 | L | L |

This custom fitting strategy offers an intermediate level of patient customization.

Another exemplary custom fitting plan employs exemplary devices of the type depicted in FIG. 7. According to this custom fitting plan. Support bases 730 and/or anchor bases 711 and/or tubing are each supplied in a fixed number of sizes (e.g. 3)

General

In an exemplary embodiment of the invention, the applicator has dimensions similar to those of a menstrual tampon.

In an exemplary embodiment of the invention, an intravaginal anti-incontinence device comprising an anchor section and a support section joined by a neck is provided. Optionally, the neck is flexible. Optionally, the device is provided encapsulated within a cover. Optionally, the device is collapsible for insertion in an applicator. Exemplary covers and applicators which are suitable for use in the context of various embodiments of the invention are described, for example, in WO2004/103213; WO2005/087514; WO2005/087513 and WO2006/097935 which are each fully incorporated herein by reference.

In an exemplary embodiment of the invention, the device is designed to lie along a long axis of the vagina and apply pressure and/or provide support when needed to one or more parts of the urethra, including optionally the bladder neck.

In an exemplary embodiment of the invention, the apparatus has one or more axes of symmetry. For example, the device can be rotationally symmetric and/or symmetric around a plane that includes the device axis. Optionally, one or both of the anchor section and support section of the device are symmetric. Optionally, a section or all of the device has a two-fold symmetry.

In an exemplary embodiment of the invention, the device is configured so that it can be inserted into the vagina and operate substantially independently of a rotational orientation thereof. For example, a rotationally symmetric device, in which the arms fall into position on either side of the urethra, may be provided. Optionally, the cover assists in rotational self orientation of the device. Optionally, the device operates within a range of 180 degrees. For example, if a side marked "up" is oriented towards a top of the body rather than a bottom of the body, the device will operate. For example, one or more support arms may be provided oriented towards the "up direction" and/or spaced apart in a manner suitable to engage and/or support the urethra and/or bladder neck.

In an exemplary embodiment of the invention, the device does not interfere with a normal flow of uterine and/or vaginal secretions to a clinically significant degree. Optionally, such non-interference is provided by using a porous cover. Optionally or alternatively, the device structure is sparse, especially from an axial view, so discharge can flow between the arms and legs of the device. Optionally, the arms and legs are designed so that if/when vaginal walls collapse on them, there is still a space between the device and the walls, for example, the collapsing of the walls not reaching a central node of the device. Optionally or alternatively, a channel is defined in the device (for example, if two or more "arms" are connected at their tips) for passage of discharge therethrough.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

In some embodiments of the invention, features described in the context of a method are applied to a device. In other embodiments of the invention, features described in the context of a device can characterize a method.

In some embodiments of the invention, a single depicted part or step is subdivided into two or more parts or steps. In other embodiments of the invention, depicted parts or steps are combined into a single part/step with the described functionality.

When used in the following claims, the terms "comprises", "includes", "have" and their conjugates mean "including but not limited to". The scope of the invention is limited only by the following claims.

The invention claimed is:

1. An apparatus for treating urinary incontinence, comprising:
  (a) a support section that provides urethral support to a urethra, wherein the support section comprises a distal end and a proximal end;
  (b) an anchoring section, wherein the anchoring section comprises a distal end and a proximal end;
  (c) a neck positioned between the support section and the anchor section, the neck connected to the proximal end of the support section and connected to the proximal end of the anchor section;
  (d) a normally open expansion mechanism hingedly connected to the distal end of the support section that urges the support section radially outwards; wherein the expansion mechanism and the support section are integrally attached to one another and wherein the integral attachment to one another comprises integral hinges;
  (e) a conversion mechanism attached to the expansion mechanism that reduces a radial outward urging of the support section; and
  wherein the support section comprises a plurality of support arms, and wherein the integral attachment of the expansion member to the support section is at the distal end of each of the plurality of support arms.

2. An apparatus according to claim 1, wherein the normally open expansion mechanism urges said support section radially outwards without a force applied from outside the apparatus.

3. An apparatus according to claim 1, wherein the conversion mechanism responds to a deforming force by axially extending, thereby causing radial collapse of the support arms.

4. An apparatus according to claim 3, wherein the normally open expansion mechanism reverts to the normally open state upon removal of the force.

5. An apparatus according to claim 1, wherein each support arm of the plurality of support arms has a distal end and said distal ends of said support arms apply sufficient force to vaginal walls to ameliorate incontinence.

6. An apparatus according to claim 1, wherein said conversion mechanism urges said support arms radially inwards in response to a force applied from outside the apparatus.

7. An apparatus according to claim 6, wherein the conversion mechanism includes a string.

8. An apparatus according to claim 1, comprising:
a loading element connected to the expansion mechanism that urges at least a portion of the expansion mechanism axially towards said anchoring section.

9. An apparatus according to claim 8, wherein the loading element comprises an elastic string adapted to a hub section of the expansion mechanism.

10. An apparatus according to claim 1, wherein said support arms are hinged.

11. An apparatus according to claim 10, wherein said support arms each comprise at least two hinges.

12. An apparatus according to claim 1, wherein said support arms are flexible.

13. An apparatus according to claim 1, wherein said urethral support is mid-urethral support.

14. An apparatus according to claim 1, wherein said apparatus is flexible.

15. An apparatus according to claim 1, wherein said urethral support includes bladder neck support.

16. An apparatus according to claim 1, comprising a cover.

17. An apparatus according to claim 16, comprising a cover collapse mechanism.

18. An apparatus according to claim 1, wherein said apparatus is rotationally symmetric.

19. An apparatus according to claim 1, wherein said apparatus is configured to operate independently of a rotational insertion angle.

20. An apparatus according to claim 1, wherein said apparatus is configured to allow passage of vaginal discharges therethrough when inserted.

21. An apparatus according to claim 1, where the conversion mechanism provides a mechanical gain such that an axial force used to activate the conversion mechanism is substantially smaller than the reduction in radial force exerted by said support section.

22. An apparatus according to claim 21, wherein substantially smaller is less than 70% of the reduction in radial force exerted by the support section.

23. An apparatus according to claim 21, wherein substantially smaller is less than 50% of the reduction in radial force exerted by the support section.

24. An apparatus according to claim 21, wherein substantially smaller is less than 40% of the reduction in radial force exerted by the support section.

25. An apparatus according to claim 21, wherein substantially smaller is less than 30% of the reduction in radial force exerted by the support section.

26. An apparatus according to claim 21, wherein substantially smaller is less than 20% of the reduction in radial force exerted by the support section.

* * * * *